United States Patent [19]

Hsu et al.

[11] Patent Number: 4,985,461

[45] Date of Patent: Jan. 15, 1991

[54] INSECTICIDAL N'-SUBSTITUTED-N,N'-DIACYLHYDRAZINES

[75] Inventors: Adam C. Hsu, Lansdale; Harold E. Aller, Norristown, both of Pa.

[73] Assignee: Rohm and Haas Company, Philadelphia, Pa.

[21] Appl. No.: 789,797

[22] Filed: Oct. 21, 1985

[51] Int. Cl.$^5$ ............................................. A01N 37/18
[52] U.S. Cl. ..................................... 514/615; 514/599
[58] Field of Search ........................ 514/615, 456, 599

[56] References Cited

U.S. PATENT DOCUMENTS

| | | | |
|---|---|---|---|
| 2,758,054 | 8/1956 | Smith et al. | 167/30 |
| 4,062,934 | 12/1977 | Tilly et al. | 424/5 |
| 4,258,059 | 3/1981 | Auerbach et al. | 564/86 |
| 4,268,511 | 5/1981 | Baronnet et al. | 424/248.87 |
| 4,547,524 | 10/1985 | Kaneko et al. | 514/594 |
| 4,550,204 | 10/1985 | Von Gentzkow et al. | 564/134 |
| 4,551,472 | 11/1985 | D'Silva | 514/477 |
| 4,564,611 | 1/1986 | Stahler et al. | 514/99 |

FOREIGN PATENT DOCUMENTS

| | | |
|---|---|---|
| 1668893 | 10/1971 | Fed. Rep. of Germany . |
| 2757584 | 8/1978 | Fed. Rep. of Germany . |
| 8005 | 7/1970 | France . |
| 1481388 | 7/1977 | United Kingdom . |
| 1573668 | 8/1980 | United Kingdom . |

OTHER PUBLICATIONS

57, *J. Pharm. Sci.*, 2011–2012 (1968).
*Chemical Abstracts*, 95:132148a (1981).
*Chemical Abstracts*, 85:142768k (1976).
*Chemical Abstracts*, 82:39589s (1975).
88, *J.A.C.S.*, 4677–4681 (1986).

*Primary Examiner*—Joseph A. Lipovsky
*Attorney, Agent, or Firm*—John Demeter; Douglas Winters; Polly Ramstad

[57] ABSTRACT

This invention relates to insecticidal compositions containing N'-substituted-N,N'-diacylhydrazines, methods of using such compositions and certain novel insecticidal N'-substituted-N,N'-diacylhydrazines.

52 Claims, No Drawings

INSECTICIDAL N'-SUBSTITUTED-N,N'-DIACYLHYDRAZINES

BACKGROUND OF THE INVENTION

This invention relates to N'-substituted-N,N'-diacylhydrazines which are useful as insecticides, compositions containing those compounds and methods of their use. Certain of the disclosed hydrazines are new compounds.

The search for compounds which have a combination of excellent insecticidal activity and low undesirable toxicity is a continuing one because of factors such as the desire for compounds exhibiting greater activity, better selectivity, low undesirable environmental impact, low production cost and effectiveness against insects resistant to many known insecticides.

Compounds of the present invention are particularly suitable for controlling plant-destructive insects in crops of cultivated plants, ornamentals and forestry.

Certain hydrazine derivatives have been disclosed in the literature.

In 25 *Aust. J. Chem.*, 523–529 (1972), several N,N'-dibenzoylhydrazine derivatives are disclosed including N'-i-propyl-; N'-n-propyl-; N'-(2-methylpropyl)-; N'-(3-methylbutyl)-; N'-benzyl- and N'-phenyl-N,N'-dibenzoylhydrazine in which one or both nitrogen atoms are alkylated or phenylated. No biological activity is disclosed for those compounds.

In 61 *Helv. Chim. Acta*, 1477–1510 (1978), several N,N'-dibenzoylhydrazine and hydrazide derivatives including N'-t-butyl-N-benzoyl-N'-(4-nitrobenzoyl)hydrazine are disclosed. No biological activity is disclosed for those compounds.

In 44 *J.A.C.S.*, 2556–2567 (1922), isopropylhydrazine $(CH_3)_2CH-NH-NH_2$, symmetrical diisopropylhydrazine, dibenzoylisopropylhydrazine and certain derivatives are disclosed. No biological activity is disclosed for those compounds.

In 44 *J.A.C.S.*, 1557–1564 (1972), isopropyl, menthyl and bornyl semicarbazides are disclosed. No biological activity is disclosed for those compounds.

In 48 *J.A.C.S.*, 1030–1035 (1926), symmetrical dimethylphenylmethylhydrazine and certain related compounds including 1,2-bis-methylphenylmethyl-4-phenylsemicarbazide are disclosed. No biological activity is disclosed for those compounds.

In 27 *Bull. Chem. Soc. Japan*, 624–627 (1954), certain hydrazine derivatives including alpha,beta-dibenzoylphenylhydrazine are disclosed. No biological activity is disclosed for those compounds.

In *J. Chem. Soc.* (C), 1531–1536 (1966), N,N'-dibenzoylphenylhydrazine and N-acetyl-N'-benzoyl-p-nitrophenylhydrazine are disclosed. No biological activity is disclosed for those compounds.

In 56B *Chem. Berichte*, 954–962 (1923), symmetrical di-isopropylhydrazines, symmetrical diisobutyl- and certain derivatives including N,N'-diisobutyldibenzoylhydrazine are disclosed. No biological activity is disclosed for those compounds.

In 590 *Annalen der Chemie*, 1–36 (1954), certain N,N'-dibenzoylhydrazine derivatives are disclosed including N'-methyl- and N'-(2-phenyl)-isopropyl-N,N'-dibenzoylhydrazine. No biological activity is disclosed for those compounds.

In *J. Chem. Soc.*, 4191–4198 (1952), N,N'-di-n-propylhydrazine, N,N'-dibenzoylhydrazine and bis-3,5-dinitrobenzoyl are disclosed. No biological activity is disclosed for those compounds.

In 32 *Zhur. Obs. Khim.*, 2806–2809 (1962), N'-2,4-methyl-2,4-pentadiene-N,N'-dibenzoylhydrazine is disclosed. No biological activity is disclosed.

In 17 *Acta. Chim. Scand.*, 95–102 (1963), 2-benzoylthiobenzyhydrazide ($C_6H_5$-CS-NHNH-CO-$C_6H_5$) and certain hydrazone and hydrazine derivatives are disclosed including 1,2-dibenzoyl-benzylhydrazine. No biological activity is disclosed for those compounds.

In 25 *Zhur. Obs. Khim*, 1719–1723 (1955), N,N'-biscyclohexylhydrazine and N,N'-dibenzoylcyclohexylhydrazine are disclosed. No biological activity is disclosed for those compounds.

In *J. Chem. Soc.*, 4793–4800 (1964), certain dibenzoylhydrazine derivatives are disclosed including tribenzoylhydrazine and N,N'-dibenzoylcyclohexylhydrazine. No biological activity is disclosed for those compounds.

In 36 *J. Prakt. Chem.*, 197–201 (1967), certain dibenzoylhydrazine derivatives including N'-ethyl-; N'-n-propyl-; N'-isobutyl-; N'-neopentyl-; N'-n-heptyl-; and N'-cyclohexylmethyl-N,N'-dibenzoylhydrazines are disclosed. No biological activity is disclosed for those compounds.

In 26 *J.O.C.*, 4336–4340 (1961) N'-t-butyl-N,N'-di-(t-butoxycarbonyl)hydrazide is disclosed. No biological activity is disclosed.

In 41 *J.O.C.*, 3763–3765 (1976), N'-t-butyl-N-(phenylmethoxycarbonyl)-N'-(chlorocarbonyl)hydrazide is disclosed. No biological activity is disclosed.

In 94 *J.A.C.S.*, 7406–7416 (1972) N'-t-butyl-N,N'-dimethoxycarbonylhydrazide is disclosed. No biological activity is disclosed.

In 43 *J.O.C.*, 808–815 (1978), N'-t-butyl-N-ethoxycarbonyl-N'-phenylaminocarbonylhydrazide and N'-t-butyl-N-ethoxycarbonyl-N'-methylaminocarbonylhydrazide are disclosed. No biological activity is disclosed for those compounds.

In 39 *J. Econ. Ent.*, 416–417 (1946), certain N-phenyl-N'-acylhydrazines are disclosed and evaluated for their toxicity against coddling moth larvae.

The N'-substituted-N,N'-diacylhydrazines of the invention differ from known compounds primarily by N'-substituent and their N,N'-diacyl substituents.

Compounds of the present invention are also distinguished by their excellent insecticidal activity against insects of the orders Lepidoptera and Coleoptera, and particularly against insects of the order Lepidoptera, without material adverse impact on beneficial insects.

SUMMARY OF THE INVENTION

In accordance with the present invention, there are provided insecticidal compositions and methods of using such compositions wherein the compositions comprise an agronomically acceptable carrier and an insecticidally effective amount of, or from about 0.0001% to about 99% by weight of the composition, a compound having the formula:

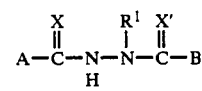

wherein
X and X' are the same or different O, S or NR;

$R^1$ is unsubstituted ($C_3$-$C_{10}$) branched alkyl or a ($C_1$-$C_4$) straight chain alkyl substituted with one or two of the same or different ($C_3$-$C_6$)-cycloalkyl; and A and B are the same or different unsubstituted naphthyl or substituted naphthyl where the substituents can be from one to three of the same or different halo; cyano; nitro; hydroxy; ($C_1$-$C_4$)alkoxy; ($C_1$-$C_4$)alkyl; carboxy; ($C_1$-$C_4$)-alkoxycarbonyl; ($C_1$-$C_4$)alkanoyloxy; amino; ($C_1$-$C_4$)alkylamino; or ($C_1$-$C_4$)dialkylamino having independently the stated number of carbon atoms in each alkyl group; unsubstituted phenyl or substituted phenyl where the substituents can be from one to five of the same or different halo; nitroso; nitro; cyano; hydroxy; ($C_1$-$C_6$)alkyl; ($C_1$-$C_6$)haloalkyl; ($C_1$-$C_6$)cyanoalkyl; ($C_1$-$C_6$)alkoxy; ($C_1$-$C_6$)haloalkoxy; ($C_1$-$C_6$)alkoxyalkyl having independently the stated number of carbon atoms in each alkyl group; ($C_1$-$C_6$)alkoxyalkoxy having independently the stated number of carbon atoms in each alkyl group carboxyoxy;; ($C_1$-$C_6$)alkoxycarbonyloxy; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkenylcarbonyl; ($C_2$-$C_6$)alkadienyl; ($C_2$-$C_6$)alkynyl optionally substituted with halo, cyano, nitro, hydroxy, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkynylcarbonyl; carboxy; ($C_1$-$C_6$)carboxyalkyl; ($C_1$-$C_6$)-alkoxycarbonylalkyl having independently the stated number of carbon atoms in each alkyl group; COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; ($C_1$-$C_6$)alkanoyloxy; amino; ($C_1$-$C_6$)alkylamino or ($C_1$-$C_6$)dialkylamino having independently the state number of carbon atoms in each alkyl group amino, ($C_1$-$C_6$)alkylamino or ($C_1$-$C_6$)dialkylamino having independently the stated number of carbon atoms in each alkyl group substituted with hydroxy, ($C_1$-$C_4$)alkoxy or ($C_1$-$C_4$)alkylthio groups; phenylamino; diphenylamino; CONRR'—OCONRR'—C(NR)NR'R" —N=NR; phenylazo; —NRCOR'—NRCO$_2$R'; —N(COR)COR'; carbonyloxy —O-CONRCOR'; sulfhydryl; halothio; thiocyanato; ($C_1$-$C_6$)alkylthio; ($C_1$-$C_6$)haloalkylthio; ($C_1$-$C_6$)-alkylsulfinyl; ($C_1$-$C_6$)alkylsulfonyl; phenyl sulfonate; ($C_1$-$C_6$)alkylsulfonate; ($C_1$-$C_6$)haloalkylsulfonyloxy; —SO$_2$NRR'; —NRSOR', —NRSO$_2$R'; ($C_1$-$C_6$)alkylthio-carbonyl; ($C_1$-$C_6$)alkydithioxate; —NRCSR'; —SCOR; $C_1$-$C_6$trialkylsilyl having independently the stated number of carbon atoms in each alkyl group; unsubstituted phenyl; phenyl substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; benzoyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxycarbonyl where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenylthio where the phenyl ring is unsubstituted or substituted with one to three of the same or different halo, cyano, nitro, hydroxy, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; —CR=N-$R^2$ where $R^2$ is hydroxy, ($C_1$-$C_4$)alkyl, ($C_1$-$C_4$)alkoxy, amino ($C_1$-$C_4$)alkylamino, ($C_1$-$C_4$)dialkylamino having independently the states number of carbon atoms in each alkyl group phenylamino, —COR, ($C_1$-$C_4$)alkoxycarbonyl, ($C_1$-$C_4$)-alkanoyloxy, benzoyl, phenoxycarbonyl or —CONRR'; or when two adjacent positions on the phenyl ring are substituted with alkoxy groups, these groups may be joined to form a 5 or 6 membered dioxolano or dioxano heterocyclic ring;

where R, R'and R" are hydrogen or ($C_1$-$C_6$)alkyl; and agronomically acceptable salts thereof.

Also in accordance with the present invention, there are provided certain novel insecticidal compounds having the formula

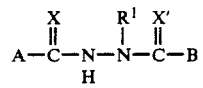

wherein

X and X' are the same or different O, S or NR;

$R^1$ is unsubstituted ($C_3$-$C_{10}$) branched alkyl or a ($C_1$-$C_4$) straight chain alkyl substituted with one or two of the same or different ($C_3$-$C_6$)-cycloalkyl; and A and B are the same or different unsubstituted naphthyl or substituted naphthyl where the substituents can be from one to three of the same or different halo; cyano; nitro; hydroxy; ($C_1$-$C_4$)alkoxy; ($C_1$-$C_4$)alkyl; carboxy; ($C_1$-$C_4$)-alkoxycarbonyl; ($C_1$-$C_4$)alkanoyloxy; amino; ($C_1$-$C_4$)alkylamino; or ($C_1$-$C_4$)dialkylamino having independently the stated number of carbon atoms in each alkyl group; unsubstituted phenyl or substituted phenyl where the substituents can be from one to five of the same or different halo; nitroso; nitro; cyano; hydroxy; ($C_1$-$C_6$)alkyl; ($C_1$-$C_6$)haloalkyl; ($C_1$-$C_6$)cyanoalkyl; ($C_1$-$C_6$)alkoxy; ($C_1$-$C_6$)halo-alkoxy; ($C_1$-$C_6$)alkoxyalkyl having independently the stated number of carbon atoms in each alkyl group; carboxyoxy ($C_1$-$C_6$)alkoxyalkoxy having independently the stated number of carbon atoms in each alkyl group; ($C_1$-$C_6$)alkoxycarbonyloxy —OCO$_2$R; ($C_2$-$C_6$)alkenyl optionally substituted with halo, cyano, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkenylcarbonyl; ($C_2$-$C_6$)alkadienyl; ($C_2$-$C_6$)alkynyl optionally substituted with halo, cyano, nitro, hydroxy, ($C_1$-$C_4$)alkyl, ($C_1$-$C_4$)alkoxy, ($C_1$-$C_4$)haloalkoxy or ($C_1$-$C_4$)alkylthio; ($C_2$-$C_6$)alkynylcarbonyl; carboxy; ($C_1$-$C_6$)carboxyalkyl; ($C_1$-$C_6$)alkoxycarbonylalkyl having independently the stated number of carbon atoms in each alkyl group; —COR; ($C_1$-$C_6$)haloalkylcarbonyl; ($C_1$-$C_6$)cyanoalkylcarbonyl; ($C_1$-$C_6$)nitroalkylcarbonyl; ($C_1$-$C_6$)alkoxycarbonyl; ($C_1$-$C_6$)haloalkoxycarbonyl; (C$_1$-C$_6$)alkanoyloxy; amino, (C$_1$-C$_6$)alkylamino or (C$_1$-C$_6$)dialkylamino having independently the stated number of carbon atoms in each alkyl group; amino, (C$_1$-C$_6$)alkylamino or (C$_1$-C$_6$)-dialkylamino having independently the stated number of carbon atoms in each alkyl group substituted with hydroxy, (C$_1$-C$_4$)alkoxy or (C$_1$-C$_4$)alkylthio groups; phenylamino; diphenylamino; —CONRR'; —OCONRR'; —C(NR)NR'R''; —N=NR; phenylazo; —NRCOR'; —NRCO$_2$R'; —N(COR)COR'; —O-CONRCOR'; sulfhydryl; halothio; thiocyanato; (C$_1$-C$_6$)alkylthio; (C$_1$-C$_6$)haloalkylthio; (C$_1$-C$_6$)alkylsulfinyl; (C$_1$-C$_6$)alkylsulfonyl; phenyl sulfonyl; (C$_1$-C$_6$)-alkylsulfonate; (C$_1$-C$_6$)haloalkyl sulfonamide —SO$_2$NRR'; alkyl —NRSOR'; —NRSO$_2$R'; (C$_1$-C$_6$)alkylthio-carbonyl; (C$_1$-C$_6$)alkyldithionate, —NRCSR$^1$; —SCOR; (C$_1$-C$_6$)trialkylsilyl having independently the stated number of carbon atoms in each alkyl group; unsubstituted phenyl; phenyl substituted with one to three of the same or different halo, cyano, nitro, hydroxy, (C$_1$-C$_4$)alkyl, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; phenoxy where the phenyl ring is unsubstituted or substituted with one to three of the same or different halo, cyano, nitro, hydroxy, (C$_1$-C$_4$)alkyl, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; benzoyl where the phenyl ring is unsubstituted or substituted with one to three of the same or different halo, cyano, nitro, hydroxy, (C$_1$-C$_4$)alkyl, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; phenoxycarbonyl where the phenyl ring is unsubstituted or substituted with one to three of the same or different halo, cyano, nitro, hydroxy, (C$_1$-C$_4$)alkyl, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; phenylthio where the phenyl ring is unsubstituted or substituted with one to three of the same or different halo, cyano, nitro, hydroxy, (C$_1$-C$_4$)alkyl, (C$_1$-C$_4$)alkoxy, carboxy, (C$_1$-C$_4$)alkoxycarbonyl, (C$_1$-C$_4$)alkanoyloxy, amino, (C$_1$-C$_4$)alkylamino or (C$_1$-C$_4$)dialkylamino having independently the stated number of carbon atoms in each alkyl group; —CR=N—R$^2$ where R$^2$ is hydroxy, (C$_1$-C$_4$)alkyl, (C$_1$-C$_4$)alkoxy, amino, (C$_1$-C$_4$)alkylamino or (C$_1$-C$_4$)dialkylamino having independently the stated number of carbon atoms in each alkyl group phenylamino, —COR, carboxy, (C$_1$-C$_4$)alkoxycarbonyl, (C$_1$-C$_4$)-alkanoyloxy, benzoyl, phenoxycarbonyl or —CONRR'; or when two adjacent positions on the phenyl ring are substituted with alkoxy groups, these groups may be joined to form a 5 or 6 membered dioxolano or dioxano heterocyclic ring;

where R, R'and R" are hydrogen or (C$_1$-C$_6$)alkyl; and agronomically acceptable salts thereof; provided that when X and X' are O, and A and B are unsubstituted phenyl, R$^1$ is not isopropyl (—CH(CH$_3$)$_2$); 2-methylpropyl (—CH$_2$CH(CH$_3$)$_2$); 3-methylbutyl (—CH$_2$CH$_2$CH(CH$_3$)$_2$); cyclohexylmethyl (—CH$_2$C$_6$H$_{11}$); or neopentyl (2,2-dimethylpropyl —CH$_2$C(CH$_3$)$_3$); and further provided that when X and X' are O, R$^1$ is t-butyl (—C(CH$_3$)$_3$) and A is unsubstituted phenyl, B is not 4-nitrophenyl.

Further, in accordance with the present invention, there are provided methods of using these compounds and compositions.

DETAILED DESCRIPTION OF THE INVENTION

The term "halo" should be understood as including chloro, fluoro, bromo and iodo. The term "alkyl" by itself or as a part of another substituent, unless otherwise stated, includes straight or branched chain groups such as methyl, ethyl, n-propyl, isopropyl, n-butyl, t-butyl, isobutyl, neopentyl and the like and where indicated higher homologues and isomers such as n-octyl, isooctyl and the like. The term "haloalkyl" by itself or as part of another substituent is an alkyl group of the stated number of carbon atoms having one or more halo atoms bonded thereto such as chloromethyl, 1- or 2-bromoethyl, trifluoromethyl and the like. Analogously, "cyanoalkyl" by itself or as part of another group is an alkyl group of the stated number of carbon atoms having one or more cyano groups bonded thereto; "haloalkoxy" by itself or as part of another group is an alkoxy group of the stated number of carbon atoms having one or more halo atoms bonded thereto such as difluoromethoxy, trifluoromethoxy, 2-fluoroethoxy, 2,2,2-trifluoroethoxy and the like. "Alkenyl" and "alkynyl" by themselves or as part of another substituent comprise straight and branched chain groups of the stated number of carbon atoms. "Alkadienyl" is a straight or branched chain alkenyl group comprising two carbon-carbon double bonds that can be conjugated such as 1,3-butadienyl, cumulated such as 1,2-propadienyl or isolated such as 1,4-pentadienyl.

Typical compounds within the scope of the present invention include, but are not limited to:

N'-t-butyl-N,N'-bis(4-chlorobenzoyl)hydrazine
N'-t-butyl-N,N'-bis(3-chlorobenzoyl)hydrazine
N'-t-butyl-N,N'-dibenzoylhydrazine
N'-t-butyl-N,N'-bis(3,4-dichlorobenzoyl)hydrazine
N'-t-butyl-N,N'-bis(4-toluoyl)hydrazine
N'-t-butyl-N,N'-bis(4-nitrobenzoyl)hydrazine
N'-t-butyl-N,N'-bis(4-anisoyl)hydrazine
N'-t-butyl-N,N'-bis(3-nitrobenzoyl)hydrazine
N'-t-butyl-N,N'-bis(3-anisoyl)hydrazine
N'-t-butyl-N,N'-bis(2-nitrobenzoyl)hydrazine
N'-t-butyl–N,N'-bis(2-chlorobenzoyl)hydrazine
N'-t-butyl-N,N'-bis(2-anisoyl)hydrazine
N'-t-butyl-N-(4-toluoyl)-N'-benzoylhydrazine
N'-t-butyl-N,N'-bis(4-cyanobenzoyl)hydrazine
N'-t-butyl-N-(4-toluoyl)-N'-(4-chlorobenzoyl)hydrazine
N'-t-butyl-N-benzoyl-N'-(4-chlorobenzoyl)hydrazine
N'-t-butyl-N-benzoyl-N'-(3-chlorobenzoyl)hydrazine
N'-t-butyl-N-benzoyl-N'-(2-chlorobenzoyl)hydrazine
N'-t-butyl-N,N'-bis(3-toluoyl)hydrazine
N'-t-butyl-N,N'-bis(2-toluoyl)hydrazine
N'-t-butyl-N-benzoyl-N'-(4-toluoyl)hydrazine
N'-t-butyl-N-benzoyl-N'-(3-toluoyl)hydrazine
N'-t-butyl-N-benzoyl-N'-(2-toluoyl)hydrazine
N'-t-butyl-N-benzoyl-N'-(4-anisoyl)hydrazine
N'-t-butyl-N-benzoyl-N'-(3-anisoyl)hydrazine
N'-t-butyl-N-benzoyl-N'-(2-anisoyl)hydrazine
N'-t-butyl-N-benzoyl-N'-(4-n-butylbenzoyl)hydrazine
N'-t-butyl-N-benzoyl-N'-(4-cyanobenzoyl)hydrazine
N'-t-butyl-N-benzoyl-N'-(4-nitrobenzoyl)hydrazine N'-t-butyl-N-benzoyl-N'-(3-nitrobenzoyl)hydrazine
N'-t-butyl-N-benzoyl-N'-(2-nitrobenzoyl)hydrazine
N'-t-butyl-N,N'-bis(4-t-butylbenzoyl)hydrazine
N'-t-butyl-N-(4-toluoyl)-N'-(3,4-dichlorobenzoyl)hydrazine
N'-t-butyl-N-benzoyl-N'-(4-fluorobenzoyl)hydrazine
N'-t-butyl-N-benzoyl-N'-(3-fluorobenzoyl)hydrazine
N'-t-butyl-N-benzoyl-N'-(2-fluorobenzoyl)hydrazine
N'-t-butyl-N-benzoyl-N'-(2,4-dichlorobenzoyl)hydrazine
N'-isopropyl-N,N'-dibenzoylhydrazine
N'-t-butyl-N-benzoyl-N'-(4-trifluoromethylbenzoyl)hydrazine
N'-t-butyl-N-benzoyl-N'-(3-trifluoromethylbenzoyl)hydrazine
N'-t-butyl-N-benzoyl-N'-(2-trifluoromethylbenzoyl)hydrazine
N'-t-butyl-N-benzoyl-N'-(2,5-difluorobenzoyl)hydrazine
N'-(2,2-dimethylethyl)-N,N'-dibenzoylhydrazine
N'-t-butyl-N-benzoyl-N'-(3-cyanobenzoyl)hydrazine
N'-(1-methylpropyl)-N,N'-dibenzoylhydrazine
N'-t-butyl-N-benzoyl-N'-(2,6-difluorobenzoyl)hydrazine
N'-t-butyl-N-(4-chlorobenzoyl)-N'-benzoylhydrazine
N'-t-butyl-N-benzoyl-N'-(3,4-dichlorobenzoyl)hydrazine
N'-t-butyl-N-benzoyl-N'-(3,5-dichlorobenzoyl)hydrazine
N'-t-butyl-N-benzoyl-N'-(2,6-dichlorobenzoyl)hydrazine
N'-t-butyl-N-(4-t-butylbenzoyl)-N'-benzoylhydrazine
N'-t-butyl-N-(2-chlorobenzoyl)-N'-benzoylhydrazine
N'-t-butyl-N-(1-naphthoyl)-N'-benzoylhydrazine
N'-t-butyl-N,N'-dinaphthoylhydrazine
N'-t-butyl-N-(3-chlorobenzoyl)-N'-benzoylhydrazine
N'-t-butyl-N-(4-chlorobenzoyl)-N'-(3,4-dichlorobenzoyl)hydrazine
N'-t-butyl-N-(2-chlorobenzoyl)-N'-(3,4-dichlorobenzoyl)hydrazine
N'-t-butyl-N-(2-toluoyl)-N'-benzoylhydrazine
N'-t-butyl-N-benzoyl-N'-(2-chloro-4-nitrobenzoyl)hydrazine
N'-t-butyl-N-benzoyl-N'-(3,5-dinitrobenzoyl)hydrazine
N'-t-butyl-N-benzoyl-N'-(2,3-dichlorobenzoyl)hydrazine
N'-(1,2,2-trimethylethyl)-N,N'-dibenzoylhydrazine
N'-t-butyl-N-benzoyl-N'-(2-chloro-5-methylbenzoyl)hydrazine
N'-t-butyl-N-benzoyl-N'-(3,5-dimethylbenzoyl)hydrazine
N'-t-butyl-N-benzoyl-N'-(2-nitro-5-methylbenzoyl)hydrazine
N'-t-butyl-N-benzoyl-N'-(2-methyl-3-chlorobenzoyl)hydrazine
N'-t-butyl-N-benzoyl-N'-(3-chloro-4-methylbenzoyl)hydrazine
N'-t-butyl-N-benzoyl-N'-(2-nitro-3-chlorobenzoyl)hydrazine
N'-t-butyl-N-benzoyl-N'-(3-methoxy-4-nitrobenzoyl)hydrazine
N'-t-butyl-N-benzoyl-N'-(2-nitro-3-methoxybenzoyl)hydrazine
N'-t-butyl-N-benzoyl-N'-(2,4-dinitrobenzoyl)hydrazine
N'-t-butyl-N-(4-chlorobenzoyl)-N'-(2-chlorobenzoyl)hydrazine
N'-t-butyl-(4-chlorobenzoyl)-N'-(3-chlorobenzoyl)hydrazine
N'-t-butyl-N-(4-chlorobenzoyl)-N'-(4-toluoyl)hydrazine
N'-t-butyl-N-(4-chlorobenzoyl)-N'-(3,5-dichlorobenzoyl)hydrazine
N'-t-butyl-N-(4-chlorobenzoyl)-N'-(2,4-dichlorobenzoyl)hydrazine
N'-t-butyl-N-(4-chlorobenzoyl)-N'-(4-trifluoromethylbenzoyl)hydrazine
N'-t-butyl-N-benzoyl-N'-(4-methanesulfonyloxybenzoyl)hydrazine
N'-t-butyl-N-benzoyl-N'-(4-isopropylbenzoyl)hydrazine
N'-t-butyl-N-benzoyl-N'-(2-acetoxybenzoyl)hydrazine
N'-t-butyl-N-benzoyl-N'-(4-ethylbenzoyl)hydrazine
N'-t-butyl-N-benzoyl-N'-(2-bromobenzoyl)hydrazine
N'-t-butyl-N-benzoyl-N'-(4-hydroxybenzoyl)hydrazine
N'-t-butyl-N-(4-toluoyl)-N'-(2-toluoyl)hydrazine
N'-t-butyl-N-(4-toluoyl)-N'-(3-toluoyl)hydrazine
N'-t-butyl-N-(4-toluoyl)-N'-(2,4-dichlorobenzoyl)hydrazine
N'-t-butyl-N-(4-toluoyl)-N'-(3,5-dichlorobenzoyl)hydrazine
N'-t-butyl-N-(4-toluoyl)-N'-(2-chlorobenzoyl)hydrazine
N'-t-butyl-N-(4-toluoyl)-N'-(4-fluorobenzoyl)hydrazine
N'-t-butyl-N-(4-toluoyl)-N'-(4-trifluoromethylbenzoyl)hydrazine
N'-t-butyl-N-(4-toluoyl)-N'-(3-chlorobenzoyl)hydrazine
N'-t-butyl-N-(4-chlorobenzoyl)-N'-(3-chlorobenzoyl)hydrazine
N'-t-butyl-N-(4-chlorobenzoyl)-N'-(4-chloromethylbenzoyl)hydrazine
N'-t-butyl-N-(4-chlorobenzoyl)-N'-(2-toluoyl)hydrazine
N'-t-butyl-N-(4-chlorobenzoyl)-N'-(3-anisoyl)hydrazine
N'-t-butyl-N-(4-chlorobenzoyl)-N'-(3-toluoyl)hydrazine
N'-t-butyl-N,N'-bis(4-fluorobenzoyl)hydrazine
N'-t-butyl-N,N'-bis(3-fluorobenzoyl)hydrazine
N'-t-butyl-N,N'-bis(2-fluorobenzoyl)hydrazine
N'-t-butyl-N,N'-bis(2-naphthoyl)hydrazine
N'-t-butyl-N-(2-bromobenzoyl)-N'-(4-ethenylbenzoyl)hydrazine
N'-t-butyl-N-(4-toluoyl)-N'-(4-ethynylbenzoyl)hydrazine
N'-t-butyl-N-[4-(1-hydroxy-2-propynyl)benzoyl]-N'-(3,4-methylenedioxybenzoyl)hydrazine
N'-t-butyl-N-(3-phenoxybenzoyl)-N'-(2-bromobenzoyl)hydrazine
N'-t-butyl-N-(2,4-dichlorobenzoyl)-N'-(4-trifluoromethoxybenzoyl)hydrazine
N'-t-butyl-N-(4-ethylbenzoyl)-N'-(2-difluoromethoxy-4-chlorobenzoyl)hydrazine
N'-isopropyl-N'-(4-chloro-2-bromobenzoyl)-N-benzoylhydrazine
N'-(2,2-dimethylethyl)-N-(3-bromomethylbenzoyl)-N'-(4-isopropyloxybenzoyl)hydrazine
N'-t-butyl-N-(4-chloromethylbenzoyl)-N'-(2-carboxybenzoyl)hydrazine
N'-(1-methylpropyl)-N-(4-carboxybenzoyl)-N'-(3,4,5-trichlorobenzoyl)hydrazine
N'-t-butyl-N-(4-propanoylbenzoyl)-N'-[4-(4-pentenyl)benzoyl]hydrazine
N'-(1,2,2-trimethylpropyl)-N-[2-(ethoxy-1-ethoxyl)benzoyl]-N'-[4-(2-ethylbutanoyl)benzoyl]hydrazine N'-t-butyl-N-(6-bromo-2-naphthoyl)-N'-(4-benzoylbenzoyl)hydrazine
N'-isopropyl-N-(4-(2-pentynoyl)benzoyl)-N'-(3-nitrobenzoyl)hydrazine
N'-t-butyl-N-(4-bromo-2-cyanobenzoyl)-N'-(6-(5-oxotetrahydronaphthoyl)hydrazine
N'-(2,2-dimethylpropyl)-N-(4-t-butyloxycarbonylbenzoyl)
N'-(4-chloro-3-trifluoromethoxybenzoyl)hydrazine
N'-t-butyl-N-(2-benzyloxycarbonylbenzoyl)-N'-(2-methoxy-4-bromobenzoyl)hydrazine
N'-t-butyl-N-(4-(2,2,2-trifluoroethoxycarbonyl)-3-methylbenzoyl-N'-(2,4-dichloro-3-hydroxybenzoyl)hydrazine
N'-isopropyl-N-(3-propanoyloxybenzoyl)-N'-(2,5-dibromobenzoyl)hydrazine
N'-(1,2,2-trimethylpropyl)-N-(4-propylbenzoyl)-N'-(3-ethoxycarbonyloxybenzoyl)hydrazine
N'-t-butyl-N-(3,5-dimethylbenzoyl)-N'-(4-t-butylcarbonyloxybenzoyl)hydrazine
N'-(1-methylpropyl)-N-(2-aminobenzoyl)-N'-(3,4-dichlorobenzoyl)hydrazine
N'-t-butyl-N-(4-chloro-2-trifluoromethoxybenzoyl)-N'-(4-methylaminobenzoyl)hydrazine
N'-t-butyl-N-(4-dimethylaminobenzoyl)-N'-(4-acetylaminobenzoyl)hydrazine
N'-t-butyl---N-(3-formylbenzoyl)-N'-(2-chloro-4-(N-hydroxyformiminoyl)benzoyl)hydrazine
N'-t-butyl-N-(2-methanesulfonylaminobenzoyl)-N'-(2-chloro-3-(1-formylidene)-2-phenylhydrazine)
N'-(1-methylpropyl)-N-(2-aminocarbonylbenzoyl)-N'-(2-chloro-4-ethylaminocarbonylbenzoyl)hydrazine
N'-isopropyl-N-(4-methyl-3-dimethylaminocarbonylbenzoyl)
N'-(4-trifluoromethylbenzoyl)hydrazine
N'-(1,2,2-trimethylpropyl)-N-(4-trifluoromethoxy-2-chlorobenzoyl)-N'-(4-methoxycarbonylaminobenzoyl)hydrazine
N'-t-butyl-N-(2-carboxymethylbenzoyl)-N'-(4-dimethylaminocarbonyloxybenzoyl)hydrazine
N'-t-butyl-N-(3-methylaminocarbonyloxybenzoyl)-N'-(2-chloro-4-(N-acetoxyaminocarbonyloxy)benzoylhydrazine
N'-isopropyl-N-(4-methoxy-3-bromobenzoyl)-N'-(4-sulfhydrylbenzoyl)hydrazine
N'-(1-methylpropyl)-N-(3-chloro-5-sulfhydrylbenzoyl)-N'-(3-phenylazobenzoyl)hydrazine
N'-(2,2-dimethylpropyl)-N-(2-methylthiobenzoyl)-N'-(2-chloro-4-(1,3-dioxolano-2-ylbenzoyl)hydrazine
N'-t-butyl-N-(3-methanesulfinylbenzoyl)-N'-(3,4,5-trimethoxybenzoyl)hydrazine
N'-(1,2,2-trimethylpropyl)-N-(3-phenylsulfonylbenzoyl)-N'-(3,4-dichlorobenzoyl)hydrazine
N'-t-butyl-N-(3-trifluoromethanesulfonyloxybenzoyl)-N'-(2-chloro-4-trichloromethylthiobenzoyl)hydrazine
N'-t-butyl-N-(2-iodobenzoyl)-N'-(4-aminosulfonyloxybenzoyl)hydrazine
N'-t-butyl-N-(2,5-dichlorobenzoyl)-N'-(4-trimethylsilylbenzoyl)hydrazine
N'-(1,2,2-trimethylpropyl)-N-(4-acetylthiobenzoyl)-N'-(3,4-dichlorobenzoyl)hydrazine
N'-t-butyl-N-(methylthiocarbonylthioxybenzoyl)-N'-(3-chloro-4-formylaminobenzoyl)hydrazine
N'-t-butyl-N-(3-methylthiocarbonylbenzoyl)-N'-(4-pentafluoroethoxybenzoyl)hydrazine N'-(t-butyl)-N-(pentafluorobenzoyl)-N'-(4-phenylaminobenzoyl)hydrazine
N'-(t-butyl)-N-(6-chlorophenylbenzoyl)-N'-(3-chloro-4-acetylaminobenzoyl)hydrazine
N'-isopropyl-N-(3-hydroxyaminobenzoyl)-N'-(4-tribromomethylbenzoyl)hydrazine
N'-(1,2,2-trimethylpropyl)-N-(4-aminocarbonylaminobenzoyl)-N'-(2-bromobenzoyl)hydrazine
N'-(1-methylpropyl)-N-(4-fluoro-3-bromochloromethylbenzoyl)-N'-(3-cyanomethylbenzoyl)hydrazine
N'-t-butyl-N-(4-propylthiobenzoyl)-N'-(3,4-dichlorobenzoyl)hydrazine
N'-t-butyl-N-(4-chloromethylcarbonylbenzoyl)-N'-(2-bromobenzoyl)hydrazine
N'-t-butyl-N-(3-trichloroethenylbenzoyl)-N'-(4-fluorobenzoyl)hydrazine
N'-isopropyl-N-(4-(1,3-dimethylbutyl)benzoyl)-N'-(2-nitro-N'-t-butyl-N-(4-nitrosobenzoyl)-N'-(2,4-dichlorobenzoyl)hydrazine
N'-t-butyl-N-(4-(N,-methylformamidinoylbenzoyl)-N'-(3-chloro-4-bromobenzoyl)hydrazine
N'-isopropyl-N-(2,6-dichlorobenzoyl)-N'-(4-trifluoromethoxybenzoyl)hydrazine
N'-t-butyl-(2,3,4-trichlorobenzoyl)-N'-(2-nitrobenzoyl)hydrazine (4-chlorosulfenylbenzoyl)hydrazine
N'-t-butyl-N-(4-allenylbenzoyl)-N,-(4-chlorobenzoyl)hydrazine
N'-t-butyl-N-benzoyl-N'-(4-bromobenzoyl)hydrazine
N'-t-butyl-N-benzoyl-N'-(3-bromobenzoyl)hydrazine
N'-t-butyl-N-benzoyl-N'-(4-n-butylbenzoyl)hydrazine
N'-t-butyl-N-(4-ethylbenzoyl)-N'-benzoyl hydrazine
N'-t-butyl-N-(3,4-dichlorobenzoyl)-N'-benzoyl hydrazine
N'-t-butyl-N-benzoyl-N'-(4-acetylbenzoyl)hydrazine
N'-(2,2-dimethylpropyl)-N-benzoyl-N'-(2-bromobenzoyl)hydrazine
N'-(2,2-dimethylpropyl)-N-benzoyl-N'-(2-nitrobenzoyl)hydrazine
N'-(2,2-dimethylpropyl)-N-benzoyl-N'-(2-methoxybenzoyl)hydrazine
N'-t-butyl-N-benzoyl-N'-(2-iodobenzoyl)hydrazine
N'-(2-methylpropyl)-N,N'-dibenzoylhydrazine
N'-isopropyl-N-benzoyl-N'-(2-bromobenzoyl)hydrazine
N'-isopropyl-N-benzoyl-N'-(3,4-dichlorobenzoyl)hydrazine
N'-t-butyl-N-benzoyl-N'-(4-phenoxybenzoyl)hydrazine
N'-t-butyl-N-(4-trifluoromethylbenzoyl)-N'-benzoylhydrazine
N'-t-butyl-N-(4-trifluoromethylbenzoyl)-N'-(3,4-dichlorobenzoyl)hydrazine
N'-dicyclopropylmethyl-N,N'-dibenzoylhydrazine
N'-t-butyl-N-benzoyl-N'-(2-chloro-4-bromobenzoyl)hydrazine
N'-t-butyl-N-(4-chlorothiobenzoyl)-N'-benzoylhydrazine
N'-t-butyl-N-benzoyl-N'-(thiobenzoyl)hydrazine
N'-t-butyl-N-benzoyl-N'-(4-phenylbenzoyl)hydrazine
N'-t-butyl-N-benzoyl-N'-(3,4,5-trimethoxybenzoyl)hydrazine
N'-(1,2,2-trimethylpropyl)-N-benzoyl-N'-(2-nitrobenzoyl)hydrazine
N'-t-butyl-N-benzoyl-N'-(3-cyanothiomethylbenzoyl)hydrazine
N'-t-butyl-N-benzoyl-N'-(3-cyanomethylbenzoyl)hydrazine
N'-(1,2,2-trimethylpropyl)-N,N'-dibenzoylhydrazine
N'-(diisopropylmethyl)-N,N'-dibenzoylhydrazine N'-(1-cyclopropylethyl)-N,N'-dibenzoylhydrazine
N'-t-butyl-N-benzoyl-N'-(4-n-butylbenzoyl)hydrazine
N'-t-butyl-N-(4-ethylbenzoyl)-N'-(3-toluoyl)hydrazine
N'-t-butyl-N-(4-ethylbenzoyl)-N'-(4-chlorobenzoyl)hydrazine
N'-t-butyl-N-(4-ethylbenzoyl)-N'-(2-nitrobenzoyl)hydrazine
N'-t-butyl-N-benzoyl-N'-(3-toluoyl)hydrazine
N'-t-butyl-N-(4-ethylbenzoyl)-N'-(3-bromobenzoyl)hydrazine
N'-t-butyl-N-(4-ethylbenzoyl)-N'-(2-iodobenzoyl)hydrazine
N'-(1,2,2-trimethylpropyl)-N-benzoyl-N'-(2-bromobenzoyl)hydrazine
N'-t-butyl-N-benzoyl-N'-(4-carbomethoxybenzoyl)hydrazine
N'-t-butyl-N-(2-bromobenzoyl)-N'-benzoylhydrazine
N'-t-butyl-N-(2-trifluoromethylbenzoyl)-N'-benzoylhydrazine
N'-t-butyl-N-benzoyl-N'-(3-iodobenzoyl)hydrazine
N'-t-butyl-N-benzoyl-N'-(2-ethylbenzoyl)hydrazine
N'-t-butyl-N-benzoyl-N'-(3-methoxymethylbenzoyl)hydrazine Because of their good insecticidal activity, compounds of the present invention for use in the insecticidal compositions and formulations include those where, independently X and X' are I or S;

$R^1$ is unsubstituted ($C_3$-$C_8$) branched alkyl or a ($C_1$-$C_4$) straight chain alkyl substituted with one or two of the same or different ($C_3$-$C_4$)-cycloalkyl;

A and B are the same or different unsubstituted naphthyl; or unsubstituted phenyl or substituted phenyl where the substituents can be from one to three of the same or different halo; nitro; cyano; ($C_1$-$C_4$)alkyl; ($C_1$-$C_4$)haloalkyl; ($C_1$-$C_4$)cyanoalkyl; ($C_1$-$C_4$);alkoxy ($C_1$-$C_4$)alkoxyalkyl having independently the stated number of carbon atoms in each alkyl group; —COR; carboxy; ($C_1$-$C_4$)alkoxycarbonyl; ($C_1$-$C_4$)alkanoyloxy; ($C_2$-$C_6$)alkenyl; ($C_2$-$C_6$)alkadienyl; ($C_2$-$C_6$)alkynyl; amino, ($C_1$-$C_4$)alkylamino or ($C_1$-$C_4$)dialkylamino having independently the state number of carbon atoms in each alkyl group thiocyanato; ($C_1$-$C_4$)alkylthio; ($C_1$-$C_4$)alkylthiocarbonyl; ($C_1$-$C_4$)-alkyldithionate; —SCOR; ($C_1$-$C_4$)trialkylsilyl having independently the stated number of carbon atoms in each alkyl group; unsubstituted; phenyl substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; phenoxy where the phenyl ring is unsubstituted or substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or when two adjacent positions on the phenyl ring are substituted with alkoxy groups, these groups may be joined to form a 5- or 6-membered dioxolano or dioxano heterocyclic ring;

where R and R'are hydrogen or ($C_1$-$C_4$)alkyl; and agronomically acceptable salts.

Insecticidal compounds of the present invention having very good activity for use in the insecticidal compositions and formulations of the present invention include those where, independently, X and X' are O or S;

$R^1$ is branched ($C_3$-$C_8$)alkyl;

A and B are the same or different unsubstituted naphthyl; unsubstituted phenyl or substituted phenyl having one to three of the same or different halo; nitro; cyano; ($C_1$-$C_4$)alkyl; ($C_1$-$C_4$)halo-alkyl; ($C_1$-$C_4$)cyanoalkyl; ($C_1$-$C_4$)alkoxy; ($C_1$-$C_4$)alkoxyalkyl having independently the stated number of carbon atoms in each alkyl group; —COR; ($C_1$-$C_4$)alkoxycarbonyl; ($C_1$-$C_4$)alkanoyloxy; thiocyanato; unsubstituted phenyl phenyl substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group; or phenoxy where the phenyl ring is unsubstituted or substituted with one or two of the same or different halo, nitro, ($C_1$-$C_4$)alkyl, ($C_1$-$C_4$)alkoxy, carboxy, ($C_1$-$C_4$)alkoxycarbonyl, ($C_1$-$C_4$)alkanoyloxy, amino, ($C_1$-$C_4$)alkylamino or ($C_1$-$C_4$)dialkylamino having independently the stated number of carbon atoms in each alkyl group where R is hydrogen or ($C_1$-$C_4$)alkyl; and agronomically acceptable salts thereof.

Because of their excellent insecticidal activity, preferred compounds of the present invention for use in the insecticidal compositions and formulations of the present invention include those where, independently, X and X' are O;

$R^1$ is branched ($C_4$-$C_7$)alkyl; and

A and B are the same or different phenyl or substituted phenyl where the substituents can be from one to three of the same or different halo, nitro, ($C_1$-$C_4$)alkyl, ($C_1$-$C_4$)alkoxy, or ($C_1$-$C_4$)haloalkyl; and agronomically acceptable salts thereof.

Because of their outstanding insecticidal activity, particularly preferred compounds of the present invention for use in the insecticidal compositions and formulations of the present invention include those where, independently, X and X' are O;

$R^1$ is t-butyl, neopentyl (2,2-dimethylpropyl) or 1,2,2-trimethylpropyl;

A and B are the same or different phenyl or substituted phenyl where the substituents can be one or two of the same or different chloro, fluoro, bromo, iodo, nitro, methyl, ethyl, methoxy or trifluoromethyl; and agronomically acceptable salts thereof.

Those N'-substituted-N,N'-diacylhydrazines of Formula I which possess acidic or basic functional groups may be further reacted to form novel salts with appropriate bases or acids. These salts also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. The ammonium salts include those in which the ammonium cation has the formula $NR^5R^6R^7R^8$ wherein each of $R^5$, $R^6$, $R^7$ and $R^8$ are independently hydrogen, hydroxy, ($C_1$-$C_4$)alkoxy, ($C_1$-$C_{20}$)alkyl, ($C_3$-$C_8$)alkenyl, ($C_3$-$C_8$)alkynyl, ($C_2$-$C_8$)hydroxyalkyl, ($C_2$-$C_8$)alkoxyalkyl, ($C_2$-$C_6$)aminoalkyl, ($C_2$-$C_6$)-haloalkyl, amino, ($C_1$-$C_4$)alkyl- or ($C_1$-$C_4$)dialkylamino, substituted or unsubstituted phenyl, substituted or unsubstituted phenylalkyl, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When $R^5$, $R^6$, $R^7$ or $R^8$ substituent in the ammonium group is a substituted phenyl or substituted phenylalkyl, the substituents on the phenyl and phenalkyl will generally be selected from halo, $(C_1-C_8)$alkyl, $(C_1-C_4)$alkoxy, hydroxy, nitro, trifluoromethyl, cyano, amino, $(C_1-C_4)$alkylthio and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, octylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate and the like.

The compounds of this invention or their precursors can be prepared according to the following processes. Process A can be used when preparing compounds according to Formula I where X and X' are both oxygen and A and B are the same (for example, both A and B are phenyl or 4-chlorophenyl) or different (for example, A is 4-methylphenyl and B is 4-bromophenyl).

Process A:

$$\underset{II}{A-\overset{O}{\overset{\|}{C}}-Cl} + NH_2NHR^1 \xrightarrow[\text{Solvent}]{\text{Base}} \underset{IV}{A-\overset{O}{\overset{\|}{C}}-NH-NHR^1} \quad \text{Step 1}$$

$$\underset{IV}{A-\overset{O}{\overset{\|}{C}}-NH-NHR^1} + \underset{V}{B-\overset{O}{\overset{\|}{C}}-Cl} \xrightarrow[\text{Solvent}]{\text{Base}} \quad \text{Step 2}$$

$$\underset{I}{A-\overset{O}{\overset{\|}{C}}-NH-\overset{R^1}{\underset{|}{N}}-\overset{O}{\overset{\|}{C}}-B}$$

where $R^1$, A and B are as defined above for Formula I and X and X' are oxygen.

Process B can be used when preparing compounds according to Formula I where X and X' are oxygen, and $R^1$, A and B are as defined above for Formula I.

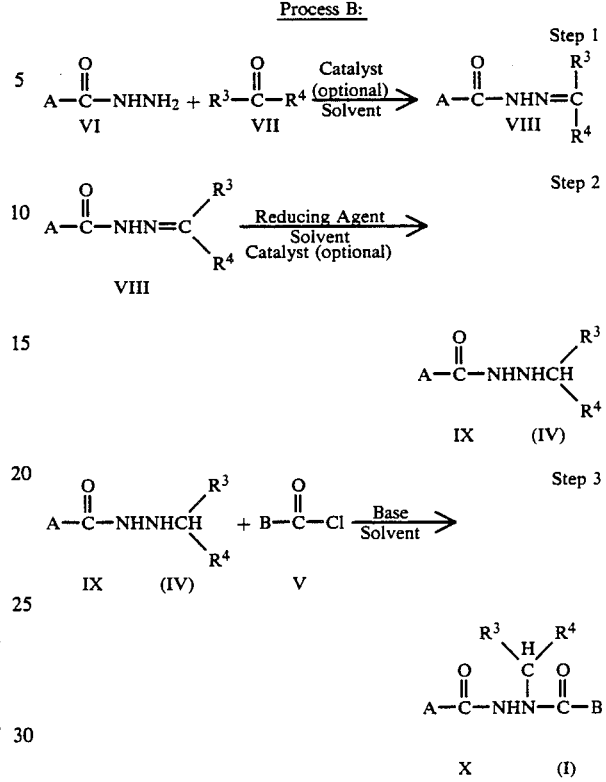

Process B:

where X and X' are oxygen, A and B are as defined above for Formula I, and $R^3$ and $R^4$ are the same or different hydrogen or $(C_2-C_9)$ straight or branched chain unsubstituted or substituted alkyl having one or two of the same or different $(C_3-C_6)$cycloalkyl provided that $R^3$ and $R^4$ are not both H or $R^3$ or $R^4$ is not a straight chain alkyl group when the other ($R^3$ or $R^4$) is hydrogen. As can be seen above, the intermediate product of Step 2, the compounds of Formula IX, corresponds to the compounds of Formula IV. In addition, the compound of Formula X corresponds to the compounds of Formula I where X and X' are oxygen.

Process C can be used when preparing compounds according to Formula I where A, B and $R^1$ are as defined for Formula I and one or both X and X' are sulfur.

Process C:

$$\underset{XI}{A-\overset{X}{\overset{\|}{C}}-Y} + \underset{III}{NH_2NHR^1} \xrightarrow[\text{Solvent}]{\text{Base}} \underset{XII}{A-\overset{X}{\overset{\|}{C}}-\underset{H}{\overset{|}{N}}-\underset{R^1}{\overset{|}{N}}H} \quad \text{Step 1}$$

$$\underset{XII}{A-\overset{X}{\overset{\|}{C}}-\underset{H}{\overset{|}{N}}-\underset{R^1}{\overset{|}{N}}H} + \underset{XIII}{B-\overset{X'}{\overset{\|}{C}}-Y} \xrightarrow[\text{Solvent}]{\text{Base}} \quad \text{Step 2}$$

$$\underset{I}{A-\overset{X}{\overset{\|}{C}}-\underset{H}{\overset{|}{N}}-\underset{R^1}{\overset{|}{N}}-\overset{X'}{\overset{\|}{C}}-B}$$

where A, B and R¹ are as defined above for Formula I and one or both X and X' are sulfur, and Y is a good leaving group such as carboxyalkylthio (for example, carboxymethylthio, —SCH$_2$CO$_2$H); alkylthio (for example, methylthio); or halo (for example, chloro).

In process A, a compound of Formula II is reacted with a monosubstituted hydrazine of Formula III or a corresponding acid addition salt such as the hydrochloride salt or the like in the presence of a base in an inert or substantially inert solvent or mixture of solvents to afford an intermediate product of Formula IV which can be isolated or further reacted with a compound of Formula V in the presence of a base in an inert or substantially inert solvent or mixture of solvents to afford the desired product of Formula I.

When A and B are the same, for example, both A and B are 4-chlorophenyl, two equivalents of a compound of Formula II or V are reacted with a monosubstituted hydrazine of Formula III in the presence of a base in an inert or substantially inert solvent or mixture of solvents to afford the desired product of Formula I.

Examples of the compounds of Formula II and/or Formula V which can be used in the above processes include benzoyl chloride, 4-chlorobenzoyl chloride, 4-methylbenzoyl chloride, 3,5-dichlorobenzoyl chloride, 2-bromobenzoyl chloride, 3-cyanobenzoyl chloride and the like. The compounds of Formula II and/or Formula V are generally commercially available or can be prepared by known procedures.

Examples of the compounds of Formula III which can be used in the above processes include isopropylhydrazine, t-butylhydrazine, neopentylhydrazine, alpha-methylneopentylhydrazine, isobutylhydrazine, isopentylhydrazine, isooctylhydrazine, and the like. The compounds of Formula III are generally commercially available or can be prepared by known procedures.

Suitable solvents for use in the above processes include water; alcohols such as methanol, ethanol, isopropanol and the like; hydrocarbons such as toluene, xylene, hexane, heptane and the like; glyme; tetrahydrofuran; acetonitrile; pyridine; or haloalkanes such as methylene chloride or mixtures of these solvents.

Preferred solvents are water, toluene, methylene chloride or a mixture of these solvents.

Examples of bases for use in the above processes include tertiary amines such as triethylamine; pyridine; potassium carbonate; sodium carbonate; sodium bicarbonate; sodium hydroxide; or potassium hydroxide. Preferred bases are sodium hydroxide, potassium hydroxide or triethylamine.

In Process B, a compound of Formula VI is reacted with a ketone or aldehyde of Formula VII in an inert or substantially inert solvent or mixture of solvents and optionally in the presence of a catalyst to afford an intermediate product of Formula VIII. The intermediate product of Formula VIII is then further reacted with a reducing agent in an inert or substantially inert solvent or mixture of solvents to afford a second intermediate product of Formula IX (IV) which can be isolated or further reacted with a compound of Formula V in the presence of a base in an inert or substantially inert solvent or mixture of solvents to afford the desired product of Formula X (I).

Examples of the compounds of Formula VI which can be used in the above Process B include benzoylhydrazine, 4-chlorobenzoylhydrazine, 2-methylbenzoylhydrazine, 4-methylbenzoylhydrazine, 3,5-dichlorobenzoylhydrazine and the like. The compounds of Formula VI are generally commercially available or can be prepared by known procedures.

Examples of the compounds of Formula VII which can be used in the above Process B include 1,1,1-trimethylacetaldehyde, methylethylketone, diethylketone and the like. The compounds of Formula VII are generally commercially available or can be prepared by known procedures.

Optionally, a catalyst may be used in Step 1 of Process B. Suitable catalysts generally include organic acids such as acetic acid, trifluoroacetic acid, oxalic acid and the like; mineral acids such as hydrochloric acid, sulfuric acid, nitric acid and the like; arylsulfonic acids such as toluenesulfonic acid; or pyridinium toluenesulfonate. Preferred catalysts are organic acids or arylsulfonic acids. Most preferred catalysts are acetic acid or trifluoroacetic acid.

Suitable solvents for use in the above Process B, Step 1, include alcohols such as methanol, ethanol, isopropanol and the like; hydrocarbons such as toluene, benzene; ethers such as tetrahydrofuran (THF), glyme and the like; or dimethylformamide. Preferred solvents are alcohols and hydrocarbons. Most preferred solvents are alcohols such as methanol or ethanol.

Examples of suitable reducing agents for use in the above Process B, Step 2, include hydrides such as sodium borohydride and derivatives thereof such as sodium cyanoborohydride, lithium aluminum hydride and derivatives thereof and the like; or diborane. Preferred reducing agents are sodium borohydride and derivatives thereof or lithium aluminum hydride and derivatives thereof. Most preferred as a reducing agent is sodium cyanoborohydride.

Optionally, in Process B, Step 2, a catalyst may be included. Examples of suitable catalysts include organic acids such as acetic acid, trifluoroacetic acid; or mineral acids such as hydrochloric acid, sulfuric acid and the like. Preferred catalysts are organic acids or hydrochloric acid. Most preferred catalysts are acetic acid, trifluoroacetic acid or hydrochloric acid.

Suitable solvents for use in the above Process B, Step 2, include alcohols such as methanol, ethanol, isopropanol and the like; ethers such as tetrahydrofuran (THF), diethylether, glyme and the like; or halohydrocarbons such as methylene chloride, chloroform and the like. Preferred solvents are alcohols and most preferred are methanol or ethanol.

Step 3 of Process B corresponds to Step 2 of Process A. Consequently, those bases and solvents suitable for use in Step 2 of Process A are suitable for use in Step 3 of Process B including the preferred bases and solvents described above.

In Process C, a compound of Formula XI is reacted with a monosubstituted hydrazine of Formula III or a corresponding acid addition salt such as the hydrochloride salt or the like in the presence of a base in an inert or substantially inert solvent or mixture of solvents to afford an intermediate compound of Formula XII which can be isolated or further reacted with a compound of Formula XIII in the presence of a base in an inert or substantially inert solvent or mixture of solvents to afford the desired product of Formula I.

When A and B are the same, for example, both A and B are unsubstituted phenyl, two equivalents of a compound Formula XI or XIII are reacted with a monosubstituted hydrazine of Formula III in the presence of a base in an inert or substantially inert solvent or mixture of solvents to afford the desired product of Formula I.

Examples of the compounds of Formula XI and/or Formula XIII which can be used in the above Process C include 3-methyl-methylthio-thiobenzoate, 4-chloromethylthio-thiobenzoate, 4-methyl-methylthio-thiobenzoate, carboxymethylthio-thiobenzoate and the like. The compounds of Formula XI and/or Formula XII are generally commercially available or can be prepared by known procedures.

Suitable solvents for use in the above Process C are generally polar high-boiling solvents such as dimethylformamide (DMF); glyme; tetrahydrofuran (THF); and pyridine. The preferred solvent is pyridine.

Suitable bases for use in the above Process C include tertiary amines such as triethylamine; and pyridine. The preferred base is pyridine.

The above processes A and B can be carried out at temperatures between about −20° C. and about 100° C. Preferably, these reactions are carried out between about −5° C. and about 50° C.

Process C can be carried out at temperatures between about 10° C. and 200° C. Preferably, this reaction is carried out between about 70° C. and about 100° C.

Preparation of the compounds of the present invention by processes A, B and C is preferably carried out at about atmospheric pressure, although higher or lower pressures can be used if desired.

Substantially equimolar amounts of reactants are preferably used in processes A, B and C, although higher or lower amounts can be used if desired.

Generally, about one equivalent of base is used per equivalent of starting material of Formula II, V, XI and/or XIII. Where the acid addition salt of the monosubstituted hydrazine of Formula III is used, one additional equivalent of base is used. For example, in Process A, when substituents A and B are the same and a monosubstituted hydrazine is used, about two equivalents of base are used since about two equivalents of a suitably substituted benzoyl chloride of Formula II or V are employed. In Process A, when substituents A and B are different and an acid addition salt of the monosubstituted hydrazines of Formula III is used, about two equivalents of base are used in Step 1 and about one equivalent of base is used in Step 2.

Modifications to the above processes may be necessary to accommodate reactive functionalities of particular A and/or B substituents. Such modifications would be apparent and known to those skilled in the art.

The agronomically acceptable salts embraced by Formula I of the invention can be prepared by reacting a metal hydroxide, a metal hydride or an amine or ammonium salt, such as a halide, hydroxide or alkoxide with a compound of Formula I having one or more hydroxy or carboxy groups or reacting a quaternary ammonium salt, such as chloride, bromide, nitrate or the like with a metal salt of a compound of Formula I in a suitable solvent. When metal hydroxides are used as reagents, useful solvents include water; ethers such as glyme and the like; dioxane; tetrahydrofuran; alcohols such as methanol, ethanol, isopropanol and the like. When metal hydrides are used as reagents, useful solvents include nonhydroxylic solvents, for example, ethers such as dioxane, glyme, diethylether and the like; tetrahydrofuran; hydrocarbons such as toluene, xylene, hexane, pentane, heptane, octane and the like; dimethylformamide, and the like. When amines are used as reagents, useful solvents include alcohols, such as methanol or ethanol; hydrocarbons, such as toluene, xylene, hexane and the like; tetrahydrofuran; glyme; dioxane; or water. When ammonium salts are used as reagents, useful solvents include water; alcohols, such as methanol or ethanol; glyme; tetrahydrofuran; or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by reacting hydrochloric, hydrobromic, sulfuric, nitric, phosphoric, acetic, propionic, benzoic or other suitable acid with a compound of Formula I having a basic functional group in a suitable solvent. Useful solvents include water, alcohols, ethers, esters, ketones, haloalkanes and the like. The particular choice of solvent will depend on the relative solubilities of the starting materials and the resulting salts and slurries rather than solutions of certain reagents may be used to obtain the salts. Generally, equivalent molar amounts of starting materials are used and the salt-forming reaction is carried out at from about −10° C. to about 100° C., preferably at about room temperature.

The following examples will further illustrate this invention but are not intended to limit it in any way. In Table I, some N'-substituted-N,N'-diacyl hydrazines of the present invention that have been made are listed. The structure of these compounds was confirmed by NMR and in some cases by IR and/or elemental analysis. Specific illustrative preparation of the compounds of Examples 1, 3, 16, 44, 102 and 103 are described after Table I.

TABLE I $$\begin{array}{c} \quad X \quad\quad R^1 \quad X' \\ \quad \| \quad H \quad | \quad \| \\ A-C-N-N-C-B \end{array}$$

| Ex. No. | X | X' | $R^1$ | A | B |
|---|---|---|---|---|---|
| 1 | O | O | —C(CH$_3$)$_3$ | —C$_6$H$_4$Cl-4 | —Cl$_6$H$_4$Cl-4 |
| 2 | O | O | —C(CH$_3$)$_3$ | —C$_6$H$_4$Cl-3 | —C$_6$H$_4$Cl-3 |
| 3 | O | O | —C(CH$_3$)$_3$ | —C$_6$H$_5$ | —C$_6$H$_5$ |
| 4 | O | O | —C(CH$_3$)$_3$ | —C$_6$H$_3$Cl$_2$-3,4 | —C$_6$H$_3$Cl$_2$-3,4 |
| 5 | O | O | —C(CH$_3$)$_3$ | —C$_6$H$_4$CH$_3$-4 | —C$_6$H$_4$CH$_3$-4 |
| 6 | O | O | —C(CH$_3$)$_3$ | —C$_6$H$_4$NO$_2$-4 | —C$_6$H$_4$NO$_2$-4 |
| 7 | O | O | —C(CH$_3$)$_3$ | —C$_6$H$_4$OCH$_3$-4 | —C$_6$H$_4$OCH$_3$-4 |
| 8 | O | O | —C(CH$_3$)$_3$ | —C$_6$H$_4$NO$_2$-3 | —C$_6$H$_4$NO$_2$-3 |
| 9 | O | O | —C(CH$_3$)$_3$ | —C$_6$H$_4$OCH$_3$-3 | —C$_6$H$_4$OCH$_3$-3 |
| 10 | O | O | —C(CH$_3$)$_3$ | —C$_6$H$_4$NO$_2$-2 | —C$_6$H$_4$NO$_2$-2 |
| 11 | O | O | —C(CH$_3$)$_3$ | —C$_6$H$_4$Cl-2 | —C$_6$H$_4$Cl-2 |

TABLE I-continued $$\underset{A-\overset{\overset{X}{\|}}{C}-\overset{H}{N}-\overset{\overset{R^1}{|}}{N}-\overset{\overset{X'}{\|}}{C}-B}{}$$

| Ex. No. | X | X' | R¹ | A | B |
|---|---|---|---|---|---|
| 12 | O | O | —C(CH₃)₃ | —C₆H₄OCH₃-2 | —C₆H₄OCH₃-2 |
| 13 | O | O | —C(CH₃)₃ | —C₆H₄CH₃-4 | —C₆H₅ |
| 14 | O | O | —C(CH₃)₃ | —C₆H₄CN-4 | —C₆H₄CN-4 |
| 15 | O | O | —C(CH₃)₃ | —C₆H₄CH₃-4 | —C₆H₄Cl-4 |
| 16 | O | O | —C(CH₃)₃ | —C₆H₅ | —C₆H₄Cl-4 |
| 17 | O | O | —C(CH₃)₃ | —C₆H₅ | —C₆H₄Cl-3 |
| 18 | O | O | —C(CH₃)₃ | —C₆H₅ | —C₆H₄Cl-2 |
| 19 | O | O | —C(CH₃)₃ | —C₆H₄CH₃-3 | —C₆H₄CH₃-3 |
| 20 | O | O | —C(CH₃)₃ | —C₆H₄CH₃-2 | —C₆H₄CH₃-2 |
| 21 | O | O | —C(CH₃)₃ | —C₆H₅ | —C₆H₄CH₃-4 |
| 22 | O | O | —C(CH₃)₃ | —C₆H₅ | —C₆H₄CH₃-3 |
| 23 | O | O | —C(CH₃)₃ | —C₆H₅ | —C₆H₄CH₃-2 |
| 24 | O | O | —C(CH₃)₃ | —C₆H₅ | —C₆H₄OCH₃-4 |
| 25 | O | O | —C(CH₃)₃ | —C₆H₅ | —C₆H₄OCH₃-3 |
| 26 | O | O | —C(CH₃)₃ | —C₆H₅ | —C₆H₄OCH₃-2 |
| 27 | O | O | —C(CH₃)₃ | —C₆H₅ | —C₆H₄C(CH₃)₃-4 |
| 28 | O | O | —C(CH₃)₃ | —C₆H₅ | —C₆H₄CN-4 |
| 29 | O | O | —C(CH₃)₃ | —C₆H₅ | —C₆H₄NO₂-4 |
| 30 | O | O | —C(CH₃)₃ | —C₆H₅ | —C₆H₄NO₂-3 |
| 31 | O | O | —C(CH₃)₃ | —C₆H₅ | —C₆H₄NO₂-2 |
| 32 | O | O | —C(CH₃)₃ | —C₆H₄C(CH₃)₃-4 | —C₆H₄C(CH₃)₃-4 |
| 33 | O | O | —C(CH₃)₃ | —C₆H₄CH₃-4 | —C₆H₃Cl₂-3,4 |
| 34 | O | O | —C(CH₃)₃ | —C₆H₅ | —C₆H₄F-4 |
| 35 | O | O | —C(CH₃)₃ | —C₆H₅ | —C₆H₄F-3 |
| 36 | O | O | —C(CH₃)₃ | —C₆H₅ | —C₆H₄F-2 |
| 37 | O | O | —C(CH₃)₃ | —C₆H₃Cl₂-3,5 | —C₆H₃Cl₂-3,5 |
| 38 | O | O | —C(CH₃)₃ | —C₆H₅ | —C₆H₃Cl₂-2,4 |
| 39 | O | O | —C(CH₃)₃ | —C₆H₅ | —C₆H₅ |
| 40 | O | O | —C(CH₃)₃ | —C₆H₅ | —C₆H₄CF₃-4 |
| 41 | O | O | —C(CH₃)₃ | —C₆H₅ | —C₆H₄CF₃-3 |
| 42 | O | O | —C(CH₃)₃ | —C₆H₅ | —C₆H₄CF₃-2 |
| 43 | O | O | —C(CH₃)₃ | —C₆H₅ | —C₆H₃F₂-2,5 |
| 44 | O | O | —CH₂C(CH₃)₃ | —C₆H₅ | —C₆H₅ |
| 45 | O | O | —C(CH₃)₃ | —C₆H₅ | —C₆H₄CN-3 |
| 46 | O | O | —CH(CH₃)CH₂CH₃ | —C₆H₅ | —C₆H₅ |
| 47 | O | O | —C(CH₃)₃ | —C₆H₅ | —C₆H₃F₂-2,6 |
| 48 | O | O | —C(CH₃)₃ | —C₆H₄Cl-4 | —C₆H₅ |
| 49 | O | O | —C(CH₃)₃ | —C₆H₅ | —C₆H₃Cl₂-3,4 |
| 50 | O | O | —C(CH₃)₃ | —C₆H₅ | —C₆H₃Cl₂-3,5 |
| 51 | O | O | —C(CH₃)₃ | —C₆H₅ | —C₆H₃Cl₂-2,6 |
| 52 | O | O | —C(CH₃)₃ | —C₆H₄C(CH₃)₃-4 | —C₆H₅ |
| 53 | O | O | —C(CH₃)₃ | —C₆H₄Cl-2 | —C₆H₅ |
| 54 | O | O | —C(CH₃)₃ | | —C₆H₅ |
| 55 | O | O | —C(CH₃)₃ | | |
| 56 | O | O | —C(CH₃)₃ | —C₆H₄Cl-3 | —C₆H₅ |
| 57 | O | O | —C(CH₃)₃ | —C₆H₄Cl-4 | —C₆H₃Cl₂-3,4 |
| 58 | O | O | —C(CH₃)₃ | —C₆H₄Cl-2 | —C₆H₃Cl₂-3,4 |
| 59 | O | O | —C(CH₃)₃ | —C₆H₄CH₃-2 | —C₆H₅ |
| 60 | O | O | —C(CH₃)₃ | —C₆H₅ | —C₆H₃Cl-2-NO₂-4 |
| 61 | O | O | —C(CH₃)₃ | —C₆H₅ | —C₆H₃(NO₂)₂-3,5 |
| 62 | O | O | —C(CH₃)₃ | —C₆H₅ | —C₆H₃Cl₂-2,3 |
| 63 | O | O | —CH(CH₃)C(CH₃)₃ | —C₆H₅ | —C₆H₅ |
| 64 | O | O | —C(CH₃)₃ | —C₆H₅ | —C₆H₃Cl-2-CH₃-5 |
| 65 | O | O | —C(CH₃)₃ | —C₆H₅ | —C₆H₃(CH₃)₂-3,5 |
| 66 | O | O | —C(CH₃)₃ | —C₆H₅ | —C₆H₃NO₂-2-CH₃-5 |
| 67 | O | O | —C(CH₃)₃ | —C₆H₅ | —C₆H₃CH₃-2-Cl-3 |
| 68 | O | O | —C(CH₃)₃ | —C₆H₅ | —C₆H₃Cl-3-CH₃-4 |
| 69 | O | O | —C(CH₃)₃ | —C₆H₅ | —C₆H₃NO₂-2-Cl-3 |
| 70 | O | O | —C(CH₃)₃ | —C₆H₅ | —C₆H₃OCH₃-3-NO₂-4 |
| 71 | O | O | —C(CH₃)₃ | —C₆H₅ | —C₆H₃NO₂-2-OCH₃-3 |
| 72 | O | O | —C(CH₃)₃ | —C₆H₅ | —C₆H₃(NO₂)₂-2,4 |
| 73 | O | O | —C(CH₃)₃ | —C₆H₄Cl-4 | —C₆H₄Cl-2 |
| 74 | O | O | —C(CH₃)₃ | —C₆H₄Cl-4 | —C₆H₄Cl-3 |
| 75 | O | O | —C(CH₃)₃ | —C₆H₄Cl-4 | —C₆H₄CH₃-4 |

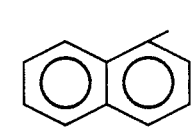

TABLE I-continued $$\underset{A-\overset{\overset{X}{\|}}{C}-\overset{H}{N}-\overset{R^1}{\underset{|}{N}}-\overset{\overset{X'}{\|}}{C}-B}{}$$

| Ex. No. | X | X' | R$^1$ | A | B |
|---|---|---|---|---|---|
| 76 | O | O | —C(CH$_3$)$_3$ | —C$_6$H$_4$Cl-4 | —C$_6$H$_3$Cl$_2$-3,5 |
| 77 | O | O | —C(CH$_3$)$_3$ | —C$_6$H$_4$Cl-4 | —C$_6$H$_3$Cl$_2$-2,4 |
| 78 | O | O | —C(CH$_3$)$_3$ | —C$_6$H$_4$Cl-4 | —C$_6$H$_4$CF$_3$-4 |
| 79 | O | O | —C(CH$_3$)$_3$ | —C$_6$H$_5$ | —C$_6$H$_4$OSO$_2$CH$_3$-4 |
| 80 | O | O | —C(CH$_3$)$_3$ | —C$_6$H$_5$ | —C$_6$H$_4$CH(CH$_3$)$_2$-4 |
| 81 | O | O | —C(CH$_3$)$_3$ | —C$_6$H$_5$ | —C$_6$H$_4$OCOCH$_3$-2 |
| 82 | O | O | —C(CH$_3$)$_3$ | —C$_6$H$_5$ | —C$_6$H$_4$CH$_2$CH$_3$-4 |
| 83 | O | O | —C(CH$_3$)$_3$ | —C$_6$H$_5$ | —C$_6$H$_4$Br-2 |
| 84 | O | O | —C(CH$_3$)$_3$ | —C$_6$H$_5$ | —C$_6$H$_4$OH-4 |
| 85 | O | O | —C(CH$_3$)$_3$ | —C$_6$H$_4$CH$_3$-4 | —C$_6$H$_4$CH$_3$-2 |
| 86 | O | O | —C(CH$_3$)$_3$ | —C$_6$H$_4$CH$_3$-4 | —C$_6$H$_4$CH$_3$-3 |
| 87 | O | O | —C(CH$_3$)$_3$ | —C$_6$H$_4$CH$_3$-4 | —C$_6$H$_3$Cl$_2$-2,4 |
| 88 | O | O | —C(CH$_3$)$_3$ | —C$_6$H$_4$CH$_3$-4 | —C$_6$H$_3$Cl$_2$-3,5 |
| 89 | O | O | —C(CH$_3$)$_3$ | —C$_6$H$_4$CH$_3$-4 | —C$_6$H$_4$Cl-2 |
| 90 | O | O | —C(CH$_3$)$_3$ | —C$_6$H$_4$CH$_3$-4 | —C$_6$H$_4$F-4 |
| 91 | O | O | —C(CH$_3$)$_3$ | —C$_6$H$_4$CH$_3$-4 | —C$_6$H$_4$CF$_3$-4 |
| 92 | O | O | —C(CH$_3$)$_3$ | —C$_6$H$_4$CH$_3$-4 | —C$_6$H$_4$Cl-3 |
| 93 | O | O | —C(CH$_3$)$_3$ | —C$_6$H$_4$Cl-4 | —C$_6$H$_4$CH$_2$Cl-3 |
| 94 | O | O | —C(CH$_3$)$_3$ | —C$_6$H$_4$Cl-4 | —C$_6$H$_4$CH$_2$Cl-4 |
| 95 | O | O | —C(CH$_3$)$_3$ | —C$_6$H$_4$Cl-4 | —C$_6$H$_4$CH$_3$-2 |
| 96 | O | O | —C(CH$_3$)$_3$ | —C$_6$H$_4$Cl-4 | —C$_6$H$_4$OCH$_3$-3 |
| 97 | O | O | —C(CH$_3$)$_3$ | —C$_6$H$_4$Cl-4 | —C$_6$H$_4$CH$_3$-3 |
| 98 | O | O | —C(CH$_3$)$_3$ | —C$_6$H$_4$F-4 | —C$_6$H$_4$F-4 |
| 99 | O | O | —C(CH$_3$)$_3$ | —C$_6$H$_4$F-3 | —C$_6$H$_4$F-3 |
| 100 | O | O | —C(CH$_3$)$_3$ | —C$_6$H$_4$F-2 | —C$_6$H$_4$F-2 |
| 101 | O | O | —C(CH$_3$)$_3$ |  |  |
| 102 | S | O | —C(CH$_3$)$_3$ | —C$_6$H$_4$Cl-4 | —C$_6$H$_5$ |
| 103 | O | S | —C(CH$_3$)$_3$ | —C$_6$5 | —C$_6$H$_5$ |
| 104 | O | O | —C(CH$_3$)$_3$ | —C$_6$H$_5$ | —C$_6$H$_4$Br-4 |
| 105 | O | O | —C(CH$_3$)$_3$ | —C$_6$H$_5$ | —C$_6$H$_4$Br-3 |
| 106 | O | O | —C(CH$_3$)$_3$ | —C$_6$H$_5$ | —C$_6$H$_4$-CH$_2$CH$_2$CH$_2$CH$_3$-4 |
| 107 | O | O | —C(CH$_3$)$_3$ | —C$_6$H$_4$CH$_2$CH$_3$-4 | —C$_6$H$_5$ |
| 108 | O | O | —C(CH$_3$)$_3$ | —C$_6$H$_3$Cl$_2$-3,4 | —C$_6$H$_5$ |
| 109 | O | O | —C(CH$_3$)$_3$ | —C$_6$H$_5$ | —C$_6$COCH$_3$-4 |
| 110 | O | O | —CH$_2$-C(CH$_3$)$_3$ | —C$_6$H$_5$ | —C$_6$H$_4$Br-2 |
| 111 | O | O | —C(CH$_2$-C(CH$_3$)$_3$ | —C$_6$H$_5$ | —C$_6$H$_4$NO$_2$-2 |
| 112 | O | O | —CH$_2$-C(CH$_3$)$_3$ | —C$_6$H$_5$ | —C$_6$H$_4$OCH$_3$-2 |
| 113 | O | O | —C(CH$_3$)$_3$ | —C$_6$H$_5$ | —C$_6$H$_4$I-2 |
| 114 | O | O | —CH$_2$CH(CH$_3$)$_2$ | —C$_6$H$_5$ | —C$_6$H$_5$ |
| 115 | O | O | —CH(CH$_3$)$_2$ | —C$_6$H$_5$ | —C$_6$H$_5$ |
| 116 | O | O | —CH(CH$_3$)$_2$ | —C$_6$H$_5$ | —C$_6$H$_3$Cl$_2$-3,4 |
| 117 | O | O | —C(CH$_3$)$_3$ | —C$_6$H$_5$ | —C$_6$H$_4$OC$_6$H$_5$-4 |
| 118 | O | O | —C(CH$_3$)$_3$ | —C$_6$H$_4$CF$_3$-4 | —C$_6$H$_5$ |
| 119 | O | O | —C(CH$_3$)$_3$ | —C$_6$H$_4$CF$_3$-4 | —C$_6$H$_3$Cl$_2$-3,4 |
| 120 | O | O | 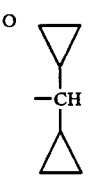 | —C$_6$H$_5$ | —C$_6$H$_5$ |
| 121 | O | O | —C(CH$_3$)$_3$ | —C$_6$H$_5$ | —C$_6$H$_3$Cl-2-Br-4 |
| 122 | O | O | —C(CH$_3$)$_3$ | —C$_6$H$_5$ | —C$_6$H$_4$C$_6$H$_5$-4 |
| 123 | O | O | —C(CH$_3$)$_3$ | —C$_6$H$_5$ | —C$_6$H$_2$(OCH$_3$)$_3$-3,4,5 |
| 124 | O | O | —CH(CH$_3$)C(CH$_3$)$_3$ | —C$_6$H$_5$ | —C$_6$H$_4$NO$_2$-2 |
| 125 | O | O | —C(CH$_3$)$_3$ | —C$_6$H$_5$ | —C$_6$H$_4$CH$_2$SCN-3 |
| 126 | O | O | —C(CH$_3$)$_3$ | —C$_6$H$_5$ | —C$_6$H$_4$CH$_2$CN-3 |
| 127 | O | O | —CH(CH$_3$)C(CH$_3$)$_3$ | —C$_6$H$_5$ | —C$_6$H$_5$ |
| 128 | O | O | —CH[CH(CH$_3$)$_2$]$_2$ | —C$_6$H$_5$ | —C$_6$H$_5$ |
| 129 | O | O | 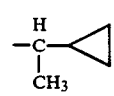 | —C$_6$H$_5$ | —C$_6$H$_5$ |
| 130 | O | O | —C(CH$_3$)$_3$ | —C$_6$H$_4$CH$_2$CH$_3$-4 | —C$_6$H$_4$CH$_3$-3 |

TABLE I-continued $$\underset{A-C-N-N-C-B}{\overset{X\phantom{xxx}R^1\phantom{x}X'}{\overset{\|\phantom{x}H\phantom{x}|\phantom{x}\|}{}}}$$

| Ex. No. | X | X' | R¹ | A | B |
|---|---|---|---|---|---|
| 131 | O | O | —C(CH₃)₃ | —C₆H₄CH₂CH₃-4 | —C₆H₄Cl-4 |
| 132 | O | O | —C(CH₃)₃ | —C₆H₄CH₂CH₃-4 | —C₆H₄NO₂-2 |
| 133 | O | O | —C(CH₃)₃ | —C₆H₅ | —C₆H₄CH₂CH₃-3 |
| 134 | O | O | —C(CH₃)₃ | —C₆H₄CH₂CH₃-4 | —C₆H₄Br-3 |
| 135 | O | O | —C(CH₃)₃ | —C₆H₄CH₂CH₃-4 | —C₆H₄I-2 |
| 136 | O | O | —CH(CH₃)C(CH₃)₃ | —C₆H₅ | —C₆H₄Br-2 |
| 137 | O | O | —C(CH₃)₃ | —C₆H₅ | —C₆H₄CO₂CH₃-4 |
| 138 | O | O | —C(CH₃)₃ | —C₆H₄Br-2 | —C₆H₅ |
| 139 | O | O | —C(CH₃)₃ | —C₆H₄CF₃-2 | —C₆H₅ |
| 140 | O | O | —C(CH₃)₃ | —C₆H₅ | —C₆H₄I-3 |
| 141 | O | O | —C(CH₃)₃ | —C₆H₅ | —C₆H₄CH₂CH₃-2 |
| 142 | O | O | —C(CH₃)₃ | —C₆H₅ | —C₆H₄CH₂OCH₃-3 |

EXAMPLE NO. 1

Preparation of N'-t-butyl-N,N'-(4-chlorobenzoyl)hydrazine

A suspension of t-butylhydrazine hydrochloride (12.5 g, 0.1 mole) in toluene (100 ml) at 0°–5° C. was treated slowly with 1 equivalent of NaOH solution, prepared from diluting 8 g of 50% NaOH commercially available solution to 20 ml of the volume with H₂O. At 0° to 5° C. with mechanical stirring, 2 equivalents of 4-chlorobenzoyl chloride (35.9 g, 0.2 mole) and 2 equivalents of NaOH (16 g of 50% NaOH diluted with H₂O to 40 ml) were added dropwise separately and simultaneously from dropping funnels. The exothermic reaction was cooled down by an ice-water bath through the entire addition. After the addition was completed, the resulting suspension was stirred at room temperature (RT) for one hour. The white precipitate (p.p.t.) was collected by suction-filtration and washed with a small amount of toluene and 100 ml of H₂O. The material was then air-dried, then crystallized from 95% aqueous CH₃OH to afford 24.65 g of N'-t-butyl-N,N'-(4-chlorobenzoyl)hydrazine as needles: m.p. 246°–248° C.

Additional product can be obtained by concentrating the mother liquor of crystallization.

EXAMPLE NO. 3

Preparation of N'-t-butyl-N,N'-dibenzoylhydrazine

To a stirred suspension of t-butylhydrazine hydrochloride (1.24 g, 10 mmoles) in toluene (50 ml) at room temperature, was added dropwise a solution of 50% aqueous sodium hydroxide (0.8 g, 10 ml). After 15 minutes, the reaction mixture was cooled to 5° C. and solutions of benzoyl chloride (2.82 gm, 20 ml) in toluene (7 ml) and 50% aqueous sodium hydroxide (1.6 g) were added dropwise and simultaneously from separate addition funnels while maintaining the temperature below 10° C. Following the addition, the reaction mixture was warmed to room temperature and stirred for 1 hr. The reaction mixture was diluted with ether and the product isolated by filtration. The product was washed with water and ether and dried. The product was recrystallized from ether-methanol to afford N'-t-butyl-N,N'-dibenzoylhydrazine as a white powder: m.p. 174°–176° C.

EXAMPLE NO. 16

Preparation of N'-t-butyl-N'-(4-chlorobenzoyl)-N-benzoylhydrazine

To a stirred suspension of t-butylhydrazine hydrochloride (1.24 g, 10 mmoles) in toluene (30 ml) at room temperature was added dropwise a 50% aqueous solution of sodium hydroxide (0.8 g, 10 mmole). After 15 min., the reaction mixture was cooled to 5° C. and a solution of benzoyl chloride (1.42 g, 10 mmole) in toluene (5 ml) and a solution of aqueous 50% sodium hydroxide (0.8 g, 10 mmole) were added dropwise simultaneously from separate addition funnels while maintaining the temperature at or below 10°. Following the addition, the reaction mixture was warmed to room temperature and stirred for 1 hr. The reaction mixture was diluted with toluene washed with water. The organic layer was separated, dried over anhydrous magnesium sulfate, and the solvent removed under vacuum to afford a yellow oil which slowly solidifies on standing. The product was recrystallized from ether-hexane to afford white crystals.

To a stirred solution of the monobenzoylated compound (1.92 g, 10 mmoles) in toluene (30 ml) at 5° C., were added dropwise simultaneously from separate addition funnels, solutions of p-chlorobenzoyl chloride (1.75 g, 10 mmoles) in toluene (5 ml) and aqueous 50% sodium hydroxide solution (0.8 g) while maintaining the temperature below 10° C. Following the addition, the reaction mixture was warmed to room temperature and stirred for 1 hr. The mixture was then diluted with hexane and the precipitated product isolated by filtration. The product was washed with water and hexane and dried. The crude product was recrystallized from ether-methanol to afford N'-t-butyl-N'-(4-chlorobenzoyl)-N-benzoylhydrazine as a white powder: m.p. 201°–204° C.

EXAMPLE NO. 44

Preparation of N'-neopentyl-N,N'-dibenzoylhydrazine

A solution of benzoylhydrazine (1.36 g, 10 mmoles), 1,1,1-trimethylacetaldehyde (0.86 g, 10 mmoles), and acetic acid (catalytic amount) in methanol are stirred at room temperature until hydrazone formation is complete. The reaction mixture is brought to a pH of 4 and sodium cyanoborohydride (0.75 g, 12.5 mmoles) is added slowly portionwise (the reaction is connected to an aqueous sodium hydroxide trap). Upon completion, the reaction is diluted with excess aqueous sodium hydroxide and the methanol is removed under vacuum. The product is partitioned into methylene chloride and washed with aqueous base and water. The organic layer is separated and dried over anhydrous magnesium sulfate. The magnesium sulfate is filtered, and the methylene chloride removed under vacuum to afford the product as a yellow oil which solidifies on standing. The crude 2-neopentyl-1-benzoylhydrazine is benzoylated directly.

To a stirred solution of the 2-neopentyl-1-benzoylhydrazine in toluene (40 ml) at 5° C., were added dropwise and simultaneously solutions of benzoyl chloride (1.4 g, 10 mmoles) in toluene (5 ml) and aqueous 50% sodium hydroxide solution (0.8 g) while maintaining the temperature below 10° C. After the addition, the reaction mixture was warmed to room temperature and stirred for 1 hour. The reaction mixture was diluted with hexane and the precipitated product isolated by filtration. The product was washed with water and hexane and dried. The crude product was recrystallized from methanol to afford N'-neopentyl-N,N'-dibenzoylhydrazine as a white powder: m.p 237°-239° C.

EXAMPLE NO. 102

Preparation of N'-t-butyl-N'-benzoyl-N-4-chlorothiobenzoylhydrazine

A mixture of 4-chloro-methylthio-thiobenzoate (3.0 g, 0.015 mol) and t-butyl hydrazine hydrochloride (2.0 g, 0.016 mol) in 5 ml of pyridine was heated at 90° C. for 18 hours. The mixture was poured into 0.1 N HCl/ether. The layers were separated and the organic extracts were washed with 3 portions of 0.1 N HCl followed by saturated aqueous NaHCO. After the extracts were dried over anhydrous magnesium sulfate, the solvents were removed under vacuum to afford 1.9 g of a brown solid. Chromatography on silica gel using ether (25%)-methylene chloride (25%)-hexane as eluant afforded 0.8 g of a golden yellow solid. The solid was dissolved in 3 ml of methylene chloride and treated with pyridine (1 ml) and benzoyl chloride (0.6 ml). After 24 hours at 23° C., the reaction mixture was poured onto 0.1 N HCl/ether. The organic layer was washed with saturated aqueous sodium bicarbonate and was dried over anhydrous magnesium sulfate. Evaporation of solvents gave a yellow oil which was chromatographed on silica gel using ether (25%)-methylene chloride (25%)-hexane as eluant to give 0.15 g of N'-t-butyl-N'-benzoyl-N-4-chlorothiobenzoylhydrazine as a yellow solid: m.p. 160°-162° C.

EXAMPLE NO. 103

Preparation of N'-t-butyl-N'-thiobenzoyl-N-benzoylhydrazine

A mixture of N'-t-butyl-N-benzoyl hydrazine (60% purity, 1.0 g, 0.0031 mol) and S-(thiobenzoyl)-thioglycolic acid (1.0 g, 0.0047 mol) in 3 ml of pyridine was heated at about 90° C. for 24 hours. The dark colored mixture was cooled and poured into 0.1 N HCl/ether. The organic layer was washed with three 15 ml portions of 0.1 N HCl followed by saturated aqueous sodium bicarbonate. The organic extracts were dried over anhydrous magnesium sulfate. Evaporation of the solvents afforded 0.5 g of a brown oil which was recrystallized from ether-hexane to yield 0.2 g of N'-t-butyl-N'-thiobenzoyl-N-benzoylhydrazine as a tan solid m.p. 169°-171° C.

By following substantially the procedures in Examples 1 and 3 and using the reactants shown below in Table II the products of Example Nos. 2, 4 through 12, 14, 19, 20, 32, 37, 55 and 98 through 101 were prepared.

TABLE II

| Ex. No. | Compound of Formula II or V | Compound of Formula III | Base | Solvent | m.p. |
|---|---|---|---|---|---|
| 2 | 3-chlorobenzoyl chloride | t-butylhydrazine hydrochloride | sodium hydroxide | toluene and water | 207–208° C. |
| 4 | 3,4-dichlorobenzoyl chloride | t-butylhydrazine hydrochloride | sodium hydroxide | toluene and water | 225–227° C. |
| 5 | 4-ethylbenzoyl chloride | t-butylhydrazine hydrochloride | sodium hydroxide | toluene and water | 222–223° C. |
| 6 | 4-nitrobenzoyl chloride | t-butylhydrazine hydrochloride | sodium hydroxide | toluene and water | 237–240° C. |
| 7 | 4-methoxybenzoyl chloride | t-butylhydrazine hydrochloride | sodium hydroxide | toluene and water | 210–211° C. |
| 8 | 3-nitrobenzoyl chloride | t-butylhydrazine hydrochloride | sodium hydroxide | toluene and water | 225–227° C. |
| 9 | 3-methoxybenzoyl chloride | t-butylhydrazine hydrochloride | sodium hydroxide | toluene and water | 164–166° C. |
| 10 | 2-nitrobenzoyl chloride | t-butylhydrazine hydrochloride | sodium hydroxide | toluene and water | 228–230° C. |
| 11 | 2-chlorobenzoyl chloride | t-butylhydrazine hydrochloride | sodium hydroxide | toluene and water | 217–218° C. |
| 12 | 2-!ethoxybenzoyl chloride | t-butylhydrazine hydrochloride | sodium hydroxide | toluene and water | 96–97° C. |
| 14 | 4-cyanobenzoyl chloride | t-butylhydrazine hydrochloride | sodium hydroxide | toluene and water | 241–244° C. |
| 19 | 3-methylbenzoyl chloride | t-butylhydrazine hydrochloride | sodium hydroxide | toluene and water | 146–148° C. |
| 20 | 2-methylbenzoyl chloride | t-butylhydrazine hydrochloride | sodium hydroxide | toluene and water | 194–195° C. |
| 32 | 4-t-butylbenzoyl chloride | t-butylhydrazine hydrochloride | sodium hydroxide | toluene and water | 194–196° C. |
| 37 | 3,5-dichlorobenzoyl chloride | t-butylhydrazine hydrochloride | sodium hydroxide | toluene and water | |
| 55 | 1-naphthtoylchloride | t-butylhydrazine hydrochloride | sodium hydroxide | toluene and water | 105–108° C. |
| 98 | 4-fluorobenzoyl chloride | t-butylhydrazine hydrochloride | sodium hydroxide | toluene and water | 210–214° C. |
| 99 | 3-fluorobenzoyl | t-butylhydrazine | sodium | toluene | 130– |

TABLE II-continued

| Ex. No. | Compound of Formula II or V | Compound of Formula III | Base | Solvent | m.p. |
|---|---|---|---|---|---|
|  | chloride | hydrochloride | hydroxide | and water | 145° C. |
| 100 | 2-fluorobenzoyl chloride | t-butylhydrazine hydrochloride | sodium hydroxide | toluene and water | 141–145° C. |
| 101 | 2-naphthoylchloride | t-butylhydrazine hydrochloride | sodium hydroxide | toluene and water | 246–249° C. |

By following substantially the procedures in Example 16 and using the reactants shown below in Table III, the products of Example Nos. 13, 15, 17, 18, 21 through 31, 33 through 36, 38, 40 through 43, 45, 47 through 54, 57 through 62, 64 through 97, 104 through 109, 113, 117, 118, 119, 121, 122, 123, 125, 126, 130 through 135 and 137 through 142 were prepared.

TABLE III

| Example No. | Compound of Formula II | Compound of Formula V | Compound of Formula III | Base | Solvents | m.p. |
|---|---|---|---|---|---|---|
| 17 | benzoylchloride | 3-chlorobenzoyl chloride | t-butylhydrazine hydrochloride | sodium hydroxide | toluene and water | 177–179° C. |
| 18 | benzoylchloride | 2-chlorobenzoyl chloride | t-butylhydrazine hydrochloride | sodium hydroxide | toluene and water | 182–184° C. |
| 21 | benzoylchloride | 4-methylbenzoyl chloride | t-butylhydrazine hydrochloride | sodium hydroxide | toluene and water | 177–179° C. |
| 22 | benzoylchloride | 3-methylbenzoyl chloride | t-butylhydrazine hydrochloride | sodium hydroxide | toluene and water | 198–200° C. |
| 23 | benzoylchloride | 2-methylbenzoyl chloride | t-butylhydrazine hydrochloride | sodium hydroxide | toluene and water | 200–202° C. |
| 24 | benzoylchloride | 4-methoxybenzoyl chloride | t-butylhydrazine hydrochloride | sodium hydroxide | toluene and water | 214–216° C. |
| 25 | benzoylchloride | 3-methoxybenzoyl chloride | t-butylhydrazine hydrochloride | sodium hydroxide | toluene and water | 178.5–181° C. |
| 26 | benzoylchloride | 2-methoxybenzoyl chloride | t-butylhydrazine hydrochloride | sodium hydroxide | toluene and water | 175–177° C. |
| 27 | benzoylchloride | 4-t-butylbenzoyl chloride | t-butylhydrazine hydrochloride | sodium hydroxide | toluene and water | 185–188° C. |
| 28 | benzoylchloride | 4-cyanobenzoyl chloride | t-butylhydrazine hydrochloride | sodium hydroxide | toluene and water | 185–190° C. |
| 29 | benzoylchloride | 4-nitrobenzoyl chloride | t-butylhydrazine hydrochloride | sodium hydroxide | toluene and water | 216–218° C. |
| 30 | benzoylchloride | 3-nitrobenzoyl chloride | t-butylhydrazine hydrochloride | sodium hydroxide | toluene and water | 194–198° C. |
| 31 | benzoylchloride | 2-nitrobenzoyl chloride | t-butylhydrazine hydrochloride | sodium hydroxide | toluene and water | 135–137° C. |
| 33 | 4-methylbenzoyl chloride | 3,4-dichlorobenzoyl chloride | t-butylhydrazine hydrochloride | sodium hydroxide | toluene and water | 238–240° C. |
| 34 | benzoylchloride | 4-fluorobenzoyl chloride | t-butylhydrazine hydrochloride | sodium hydroxide | toluene and water | 202–203° C. |
| 35 | benzoylchloride | 3-fluorobenzoyl chloride | t-butylhydrazine hydrochloride | sodium hydroxide | toluene and water | 155–158° C. |
| 36 | benzoylchloride | 2-fluorobenzoyl chloride | t-butylhydrazine hydrochloride | sodium hydroxide | toluene and water | 168–170° C. |
| 38 | benzoylchloride | 2,4-dichlorobenzoyl chloride | t-butylhydrazine hydrochloride | sodium hydroxide | toluene and water | 82–84° C. |
| 40 | benzoylchloride | 4-trifluoromethyl benzoylchloride | t-butylhydrazine hydrochloride | sodium hydroxide | toluene and water | 216–218° C. |
| 41 | benzoylchloride | 3-trifluoromethyl benzoylchloride | t-butylhydrazine hydrochloride | sodium hydroxide | toluene and water | 186–190° C. |
| 42 | benzoylchloride | 2-trifluoromethyl benzoylchloride | t-butylhydrazine hydrochloride | sodium hydroxide | toluene and water | 163–165° C. |
| 43 | benzoylchloride | 2,5-difluorobenzoyl chloride | t-butylhydrazine hydrochloride | sodium hydroxide | toluene and water | 147–150° C. |
| 45 | benzoylchloride | 3-cyanobenzoyl chloride | t-butylhydrazine hydrochloride | sodium hydroxide | toluene and water | 138–140° C. |
| 47 | benzoylchloride | 2,6-difluorobenzoyl chloride | t-butylhydrazine hydrochloride | sodium hydroxide | toluene and water | 179–182° C. |
| 49 | benzoylchloride | 3,4-dichlorobenzoyl chloride | t-butylhydrazine hydrochloride | sodium hydroxide | toluene and water | 211–213° C. |
| 50 | benzoylchloride | 3,5-dichlorobenzoyl chloride | t-butylhydrazine hydrochloride | sodium hydroxide | toluene and water | >250° C. |
| 51 | benzoylchloride | 2,6-dichlorobenzoyl chloride | t-butylhydrazine hydrochloride | sodium hydroxide | toluene and water | 183–185° C. |
| 52 | 4-t-butylbenzoyl chloride | benzoylchloride | t-butylhydrazine hydrochloride | sodium hydroxide | toluene and water | glassy solid |
| 53 | 2-chlorobenzoyl chloride | benzoylchloride | t-butylhydrazine hydrochloride | sodium hydroxide | toluene and water | glassy solid |
| 54 | 1-naphthoylchloride | benzoylchloride | t-butylhydrazine hydrochloride | sodium hydroxide | toluene and water | 212–214° C. |
| 56 | 3-chlorobenzoyl chloride | benzoylchloride | t-butylhydrazine hydrochloride | sodium hydroxide | toluene and water | 182–183° C. |
| 57 | 4-chlorobenzoyl chloride | 3,4-dichlorobenzoyl chloride | t-butylhydrazine hydrochloride | sodium hydroxide | toluene and water | 261–263° C. |

TABLE III-continued

| Example No. | Compound of Formula II | Compound of Formula V | Compound of Formula III | Base | Solvents | m.p. |
|---|---|---|---|---|---|---|
| 58 | 2-chlorobenzoyl chloride | 3,4-dichlorobenzoyl chloride | t-butylhydrazine hydrochloride | sodium hydroxide | toluene and water | 256–258° C. |
| 59 | 2-methylbenzoyl chloride | benzoylchloride | t-butylhydrazine hydrochloride | sodium hydroxide | toluene and water | 182–185° C. |
| 60 | benzoylchloride | 2-chloro-4-nitro benzoylchloride | t-butylhydrazine hydrochloride | sodium hydroxide | toluene and water | glassy solid |
| 61 | benzoylchloride | 3,5-dinitrobenzoyl chloride | t-butylhydrazine hydrochloride | sodium hydroxide | toluene and water | 223–226° C. |
| 62 | benzoylchloride | 2,3-dichlorobenzoyl chloride | t-butylhydrazine hydrochloride | sodium hydroxide | toluene and water | 185–188° C. |
| 64 | benzoylchloride | 2-chloro-5-methyl benzoylchloride | t-butylhydrazine hydrochloride | sodium hydroxide | toluene and water | 212–214° C. |
| 65 | benzoylchloride | 3,5-dimethylbenzoyl chloride | t-butylhydrazine hydrochloride | sodium hydroxide | toluene and water | 194–197° C. |
| 66 | benzoylchloride | 2-nitro-5-methyl benzoylchloride | t-butylhydrazine hydrochloride | sodium hydroxide | toluene and water | 190–195° C. |
| 67 | benzoylchloride | 2-methyl-3-chloro benzoylchloride | t-butylhydrazine hydrochloride | sodium hydroxide | toluene and water | 207–209° C. |
| 68 | benzoylchloride | 3-chloro-4-methyl benzoylchloride | t-butylhydrazine hydrochloride | sodium hydroxide | toluene and water | glassy solid |
| 69 | benzoylchloride | 2-nitro-3-chloro benzoylchloride | t-butylhydrazine hydrochloride | sodium hydroxide | toluene and water | 80–83° C. |
| 70 | benzoylchloride | 3-methoxy-4-nitro benzoylchloride | t-butylhydrazine hydrochloride | sodium hydroxide | toluene and water | 205–207° C. |
| 71 | benzoylchloride | 2-nitro-3-methoxy benzoylchloride | t-butylhydrazine hydrochloride | sodium hydroxide | toluene and water | 158–159° C. |
| 72 | benzoylchloride | 2,4-dinitrobenzoyl chloride | t-butylhydrazine hydrochloride | sodium hydroxide | toluene and water | >250° C. |
| 73 | 4-chlorobenzoyl chloride | 2-chlorobenzoyl chloride | t-butylhydrazine hydrochloride | sodium hydroxide | toluene and water | 190–192° C. |
| 74 | 4-chlorobenzoyl chloride | 3-chlorobenzoyl chloride | t-butylhydrazine hydrochloride | sodium hydroxide | toluene and water | 195–197° |
| 75 | 4-chlorobenzoyl chloride | 4-methylbenzoyl chloride | t-butylhydrazine hydrochloride | sodium hydroxide | toluene and water | 204–205.5° C. |
| 76 | 4-chlorobenzoyl chloride | 3,5-dichlorobenzoyl chloride | t-butylhydrazine hydrochloride | sodium hydroxide | toluene and water | 215–219° C. |
| 77 | 4-chlorobenzoyl chloride | 2,4-dichlorobenzoyl chloride | t-butylhydrazine hydrochloride | sodium hydroxide | toluene and water | 185–188° C. |
| 78 | 4-chlorobenzoyl chloride | 4-trifluoromethyl benzoylchloride | t-butylhydrazine hydrochloride | sodium hydroxide | toluene and water | 257–259° C. |
| 79 | benzoylchloride | 4-methanesulfonyl benzoylchloride | t-butylhydrazine hydrochloride | sodium hydroxide | toluene and water | 180–183° C. |
| 80 | benzoylchloride | 4-isopropylbenzoyl chloride | t-butylhydrazine hydrochloride | sodium hydroxide | toluene and water | 220–224° C. |
| 81 | benzoylchloride | 2-acetoxybenzoyl chloride | t-butylhydrazine hydrochloride | sodium hydroxide | toluene and water | 154–156° C. |
| 82 | benzoylchloride | 4-ethylbenzoyl chloride | t-butylhydrazine hydrochloride | sodium hydroxide | toluene and water | glassy solid |
| 83 | benzoylchloride | 2-bromobenzoyl chloride | t-butylhydrazine hydrochloride | sodium hydroxide | toluene and water | 85–90° C. |
| 84 | benzoylchloride | 4-hydroxybenzoyl chloride | t-butylhydrazine hydrochloride | sodium hydroxide | toluene and water | 229–233° C. |
| 85 | 4-methylbenzoyl chloride | 2-methylbenzoyl chloride | t-butylhydrazine hydrochloride | sodium hydroxide | toluene and water | 207–208° C. |
| 86 | 4-methylbenzoyl chloride | 3-methylbenzoyl chloride | t-butylhydrazine hydrochloride | sodium hydroxide | toluene and water | 173–174° C. |
| 87 | 4-methylbenzoyl chloride | 2,4-dichlorobenzoyl chloride | t-butylhydrazine hydrochloride | sodium hydroxide | toluene and water | 147–148° C. |
| 88 | 4-methylbenzoyl chloride | 3,5-dichlorobenzoyl chloride | t-butylhydrazine hydrochloride | sodium hydroxide | toluene and water | 228–230° C. |
| 89 | 4-methylbenzoyl chloride | 2-chlorobenzoyl chloride | t-butylhydrazine hydrochloride | sodium hydroxide | toluene and water | 206–207° C. |
| 90 | 4-methylbenzoyl chloride | 4-fluorobenzoyl chloride | t-butylhydrazine hydrochloride | sodium hydroxide | toluene and water | 173–174° C. |
| 91 | 4-methylbenzoyl chloride | 4-trifluoromethyl chloride | t-butylhydrazine hydrochloride | sodium hydroxide | toluene and water | 147–148° C. |
| 92 | 4-methylbenzoyl chloride | 3-chlorobenzoyl chloride | t-butylhydrazine hydrochloride | sodium hydroxide | toluene and water | 158–161° C. |
| 93 | 4-chlorobenzoyl chloride | 3-chloromethyl benzoylchloride | t-butylhydrazine hydrochloride | sodium hydroxide | toluene and water | 203–204° C. |
| 94 | 4-chlorobenzoyl chloride | 4-chloromethyl benzoylchloride | t-butylhydrazine hydrochloride | sodium hydroxide | toluene and water | 216–217° C. |
| 95 | 4-chlorobenzoyl chloride | 2-methylbenzoyl chloride | t-butylhydrazine hydrochloride | sodium hydroxide | toluene and water | 190–195° C. |
| 96 | 4-chlorobenzoyl chloride | 3-methoxybenzoyl chloride | t-butylhydrazine hydrochloride | sodium hydroxide | toluene and water | 170–172° C. |
| 97 | 4-chlorobenzoyl chloride | 3-methylbenzoyl chloride | t-butylhydrazine hydrochloride | sodium hydroxide | toluene and water | 186–188° C. |
| 104 | benzoylchloride | 4-bromobenzoyl chloride | t-butylhydrazine hydrochloride | sodium hydroxide | toluene and water | 216–219° C. |

TABLE III-continued

| Example No. | Compound of Formula II | Compound of Formula V | Compound of Formula III | Base | Solvents | m.p. |
|---|---|---|---|---|---|---|
| 105 | benzoylchloride | 3-bromobenzoyl chloride | t-butylhydrazine hydrochloride | sodium hydroxide | toluene and water | 207–210° C. |
| 106 | benzoylchloride | 4-n-butylbenzoyl chloride | t-butylhydrazine hydrochloride | sodium hydroxide | toluene and water | glassy solid |
| 107 | 4-ethylbenzoyl chloride | benzoylchloride | t-butylhydrazine hydrochloride | sodium hydroxide | toluene and water | 197–200° C. |
| 108 | 3,4-dichloro-benzoylchloride | benzoylchloride | t-butylhydrazine hydrochloride | sodium hydroxide | toluene and water | 119–130° C. |
| 109 | benzoylchloride | 4-acetylbenzoyl chloride | t-butylhydrazine hydrochloride | sodium hydroxide | toluene and water | >250° C. |
| 113 | benzoylchloride | 2-iodobenzoyl chloride | t-butylhydrazine hydrochloride | sodium hydroxide | toluene and water | 80–82° C. |
| 117 | benzoylchloride | 4-phenoxybenzoyl chloride | t-butylhydrazine hydrochloride | sodium hydroxide | toluene and water | 240–250° C. |
| 118 | 4-trifluoromethyl-benzoylchloride | benzoylchloride | t-butylhydrazine hydrochloride | sodium hydroxide | toluene and water | 173–175° C. |
| 119 | 4-trifluoromethyl-benzoylchloride | 3,4-dichlorobenzoyl chloride | t-butylhydrazine hydrochloride | sodium hydroxide | toluene and water | 223–227° C. |
| 121 | benzoylchloride | 2-chloro-4-bromo-benzoylchloride | t-butylhydrazine hydrochloride | sodium hydroxide | toluene and water | glassy solid |
| 122 | benzoylchloride | 4-phenylbenzoyl chloride | t-butylhydrazine hydrochloride | sodium hydroxide | toluene and water | low melting solid |
| 123 | benzoylchloride | 3,4,5-trimethoxy-benzoylchloride | t-butylhydrazine hydrochloride | sodium hydroxide | toluene and water | 175–177° C. |
| 125 | benzoylchloride | 3-thiocyanomethyl-benzoylchloride | t-butylhydrazine hydrochloride | sodium hydroxide | toluene and water | low melting solid |
| 126 | benzoylchloride | 3-cyanomethyl-benzoylchloride | t-butylhydrazine hydrochloride | sodium hydroxide | toluene and water | 160–162° C. |
| 130 | 4-ethylbenzoyl chloride | 3-toluoylchloride | t-butylhydrazine hydrochloride | sodium hydroxide | toluene and water | low melting solid |
| 131 | 4-ethylbenzoyl chloride | 4-chlorobenzoyl chloride | t-butylhydrazine hydrochloride | sodium hydroxide | toluene and water | 196–197° C. |
| 132 | 4-ethylbenzoyl chloride | 2-nitrobenzoyl chloride | t-butylhydrazine hydrochloride | sodium hydroxide | toluene and water | low melting solid |
| 133 | benzoylchloride | 3-ethylbenzoyl chloride | t-butylhydrazine hydrochloride | sodium hydroxide | toluene and water | 141–144° C. |
| 134 | 4-ethylbenzoyl chloride | 3-bromobenzoyl chloride | t-butylhydrazine hydrochloride | sodium hydroxide | toluene and water | 171–174° C. |
| 135 | 4-ethylbenzoyl chloride | 2-iodobenzoyl chloride | t-butylhydrazine hydrochloride | sodium hydroxide | toluene and water | glassy solid |
| 137 | benzoylchloride | 4-carbomethoxy benzoylchloride | t-butylhydrazine hydrochloride | sodium hydroxide | toluene and water | 169–180° C. |
| 138 | 2-bromobenzoyl chloride | benzoylchloride | t-butylhydrazine hydrochloride | sodium hydroxide | toluene and water | 207° C. |
| 139 | 2-trifluoromethyl-benzoylchloride | benzoylchloride | t-butylhydrazine hydrochloride | sodium hydroxide | toluene and water | 212–214° C. |
| 140 | benzoylchloride | 3-iodobenzoyl chloride | t-butylhydrazine hydrochloride | sodium hydroxide | toluene and water | >250° C. |
| 141 | benzoylchloride | 2-ethylbenzoyl chloride | t-butylhydrazine hydrochloride | sodium hydroxide | toluene and water | oil |
| 142 | benzoylchloride | 3-methoxymethyl benzoylchloride | t-butylhydrazine hydrochloride | sodium hydroxide | toluene and water | oil |

By following substantially the procedures in Example 44 and using the reactants shown below in Table IV, the products of Example Nos. 39, 46, 63, 110, 111, 112, 114, 115, 116, 120, 124, 127, 128, 129 and 136 were prepared.

TABLE IV

| Ex. No. | m.p. | Reactants | |
|---|---|---|---|
| 39 | 163–164° C. | Compound of Formula VI: | Benzoylhydrazine |
| | | Compound of Formula VII: | Dimethyl ketone |
| | | Solvent: | Methanol |
| | | Catalyst: | Acetic acid |
| | | Compound of Formula VIII: | Benzoylhydrazone of acetone |
| | | Reducing Agent: | Sodium cyanoborohydride |
| | | Solvent: | Methanol |
| | | Catalyst: | Acetic acid |
| | | Compound of Formula IX (IV): | 2-isopropyl-1-benzoylhydrazine |
| | | Compound of Formula V: | Benzoylchloride |
| | | Base: | Sodium hydroxide |
| | | Solvent: | Toluene and water |
| 46 | glassy solid | Compound of Formula VI: | Benzoylhydrazine |
| | | Compound of Formula VII: | Methylethyl ketone |

TABLE IV-continued

| Ex. No. | m.p. | Reactants | |
|---|---|---|---|
| | | Solvent: | Methanol |
| | | Catalyst: | Acetic acid |
| | | Compound of Formula VIII: | Benzoylhydrazone of 2-butanone |
| | | Reducing Agent: | Sodium cyanoborohydride |
| | | Solvent: | Methanol |
| | | Catalyst: | Acetic acid |
| | | Compound of Formula IX (IV): | 2-sec-butyl-1-benzoylhydrazine |
| | | Compound of Formula V: | Benzoylchloride |
| | | Base: | Sodium hydroxide |
| | | Solvent: | Toluene and water |
| 63 | 239–242° C. | Compound of Formula VI: | Benzoylhydrazine |
| | | Compound of Formula VII: | Methyl-t-butyl ketone |
| | | Solvent: | Methanol |
| | | Catalyst: | Acetic acid |
| | | Compound of Formula VIII: | Benzoylhydrazone of methyl-t-butylketone |
| | | Reducing Agent: | Sodium cyanoborohydride |
| | | Solvent: | Methanol |
| | | Catalyst: | Acetic acid |
| | | Compound of Formula IX (IV): | 2-(1-methyl)neopentyl-1-benzoyl hydrazine |
| | | Compound of Formula V: | Benzoylchloride |
| | | Base: | Sodium hydroxide |
| | | Solvent: | Toluene and water |
| 110 | low melting solid | Compound of Formula VI: | Benzoylhydrazine |
| | | Compound of Formula VII: | 1,1,1-trimethylacetaldehyde |
| | | Solvent: | Methanol |
| | | Catalyst: | Acetic acid |
| | | Compound of Formula VIII: | Benzoylhydrazone of 1,1,1-trimethylacetaldehyde |
| | | Reducing Agent: | Sodium cyanoborohydride |
| | | Solvent; | Methanol |
| | | Catalyst: | Acetic acid |
| | | Compound of Formula IX (IV): | 2-neopentyl-1-benzoylhydrazine |
| | | Compound of Formula V: | 2-bromobenzoylchloride |
| | | Base: | Sodium hydroxide |
| | | Solvent: | Toluene and water |
| 111 | glassy solid | Compound of Formula VI: | Benzoylhydrazine |
| | | Compound of Formula VII: | 1,1,1-trimethylacetaldehyde |
| | | Solvent: | Methanol |
| | | Catalyst: | Acetic acid |
| | | Compound of Formula VIII: | Benzoylhydrazone of 1,1,1-trimethylacetaldehyde |
| | | Reducing Agent: | Sodium cyanoborohydride |
| | | Solvent: | Methanol |
| | | Catalyst: | Acetic acid |
| | | Compound of Formula IX (IV): | 2-neopentyl-1-benzoylhydrazine |
| | | Compound of Formula V: | 2-nitrobenzoylchloride |
| | | Base: | Sodium hydroxide |
| | | Solvent: | Toluene and water |
| 112 | glassy solid | Compound of Formula VI: | Benzoylhydrazine |
| | | Compound of Formula VII: | 1,1,1-trimethylacetaldehyde |
| | | Solvent: | Methanol |
| | | Catalyst: | Acetic acid |
| | | Compound of Formula VIII: | Benzoylhydrazone of 1,1,1-trimethylacetaldehyde |
| | | Reducing Agent: | Sodium cyanoborohydride |
| | | Solvent: | Methanol |
| | | Catalyst: | Acetic acid |
| | | Compound of Formula IX (IV): | 2-neopentyl-1-benzoylhydrazine |
| | | Compound of Formula V: | 2-anisoyl chloride |
| | | Base: | Sodium hydroxide |
| | | Solvent: | Toluene and water |
| 114 | 161–163° C. | Compound of Formula VI: | Benzoylhydrazine |
| | | Compound of Formula VII: | Isobutyraldehyde |
| | | Solvent: | Methanol |
| | | Catalyst: | Acetic acid |
| | | Compound of Formula VIII: | Benzoylhydrazone of isobutyraldehyde |
| | | Reducing Agent: | Sodium cyanoborohydride |
| | | Solvent: | Methanol |
| | | Catalyst: | Acetic Acid |
| | | Compound of Formula IX (IV): | 2-isobutyl-1-benzoylhydrazine |
| | | Compound of Fonmula V: | Benzoylchloride |
| | | Base: | Sodium hydroxide |
| | | Solvent: | Toluene and water |
| 115 | glassy solid | Compound of Formula VI: | Benzoylhydrazine |
| | | Compound of Formula VII: | Acetone |
| | | Solvent: | Methanol |
| | | Catalyst: | Acetic acid |

TABLE IV-continued

| Ex. No. | m.p. | Reactants | |
|---|---|---|---|
| | | Compound of Formula VIII: | Benzoylhydrazone of acetone |
| | | Reducing Agnt: | Sodiun cyanoborohydride |
| | | Solvent: | Methanol |
| | | Catalyst: | Acetic acid |
| | | Compound of Formula IX (IV): | 2-isopropyl-1-benzoylhydrazine |
| | | Compound of Formula V: | 2-bromobenzoylchloride |
| | | Base: | Sodium hydroxide |
| | | Solvent: | Toluene and water |
| 116 | 175–178° C. | Compound of Formula VI: | Benzoylhydrazine |
| | | Compound of Formula VII: | Acetone |
| | | Solvent: | Methanol |
| | | Catalyst: | Acetic acid |
| | | Compound of Formula VIII: | Benzoylhydrazone of acetone |
| | | Reducing Agent: | Sodium cyanoborohydride |
| | | Solvent: | Methanol |
| | | Catalyst: | Acetic acid |
| | | Compound of Formula IX (IV): | 2-isopropyl-1-benzoylhydrazine |
| | | Compound of Formula V: | 3,4-dichlorobenzoylchloride |
| | | Base: | Sodium hydroxide |
| | | Solvent: | Toluene and water |
| 120 | >250° C. | Compound of Formula VI: | Benzoylhydrazine |
| | | Compound of Formula VII: | Dicyclopropylketone |
| | | Solvent: | Methanol |
| | | Catalyst: | Acetic Acid |
| | | Compound of Formula VIII: | Benzoylhydrazone of dicyclopropylketone |
| | | Reducing Agent: | Sodim cyanoborohydride |
| | | Solvent: | Methanol |
| | | Catalyst: | Acetic acid |
| | | Compound of Formula IX (IV): | 2-dicyclopropylmethyl-1-benzoylhydrazine |
| | | Compound of Formula V: | Benzoylchloride |
| | | Base: | Sodium hydroxide |
| | | Solvent: | Toluene and water |
| 124 | glassy solid | Compound of Formula VI: | Benzoylhydrazine |
| | | Compound of Formula VII: | Methyl-t-butyl ketone |
| | | Solvent: | Methanol |
| | | Catalyst: | Acetic acid |
| | | Compound of Formula VIII: | Benzoylhydrazone of methyl-t-butylketone |
| | | Reducing Agent: | Sodium cyanoborohydride |
| | | Solvent: | Methanol |
| | | Catalyst: | Acetic acid |
| | | Compound of Formula IX (IV): | 2-(1,2,2-trimethylpropyl)-1-benzoylhydrazine |
| | | Compound of Formula V: | 2-nitrobenzoylchloride |
| | | Base: | Sodium hydroxide |
| | | Solvent: | Toluene and water |
| 127 | 239–242° C. | Compound of Formula VI: | Benzoylhydrazine |
| | | Compound of Formula VII: | Methyl-t-butyl ketone |
| | | Solvent: | Methanol |
| | | Catalyst: | Acetic acid |
| | | Compound of Formula VIII: | Benzoylhydrazone of methyl-t-butylketone |
| | | Reducing Agent: | Sodium cyanoborohydride |
| | | Solvent: | Methanol |
| | | Catalyst: | Acetic acid |
| | | Compound of Formula IX (IV): | 2-(1,2,2-trimethylpropyl)-1-benzoylhydrazine |
| | | Compound of Formula V: | Benzoylchloride |
| | | Base: | Sodium hydroxide |
| | | Solvent: | Toluene and water |
| 128 | 175–177° C. | Compound of Formula VI: | Benzoylhydrazine |
| | | Compound of Formula VII: | Diisopropyl ketone |
| | | Solvent: | Methanol |
| | | Catalyst: | Acetic acid |
| | | Compound of Formula VIII: | Benzoylhydrazone of diisopropylketone |
| | | Reducing Agent: | Sodium cyanoborohydride |
| | | Solvent: | Methanol |
| | | Catalyst: | Acetic acid |
| | | Compound of Formula IX (IV): | 2-diisopropylmethyl-1-benzoyl hydrazine |
| | | Compound of Formula V: | Benzoylchloride |
| | | Base: | Sodium hydroxide |
| | | Solvent: | Toluene and water |
| 129 | >250° C. | Compound of Formula VI: | Benzoylhydrazine |
| | | Compound of Formula VII: | Cyclopropylmethyl ketone |
| | | Solvent: | Methanol |
| | | Catalyst: | Acetic acid |

TABLE IV-continued

| Ex. No. | m.p. | Reactants | |
|---|---|---|---|
| | | Compound of Formula VIII: | Benzoylhydrazone of cyclopropyl-methylketone |
| | | Reducing Agent: | Sodium cyanoborohydride |
| | | Solvent: | Methanol |
| | | Catalyst: | Acetic acid |
| | | Compound of Formula IX (IV): | 2-(1-cyclopropylethyl)-1-benzoylhydrazine |
| | | Compound of Formula V: | Benzoylchloride |
| | | Base: | Sodium hydroxide |
| | | Solvent: | Toluene and water |
| 136 | 154–155.5° C. | Compound of Formula VI: | Benzoylhydrazine |
| | | Compound of Formula VII: | Methyl-t-butylketone |
| | | Solvent: | Methanol |
| | | Catalyst: | Acetic acid |
| | | Compound of Formula VIII: | Benzoylhydrazone of methyl-t-butylketone |
| | | Reducing Agent: | Sodium cyanoborohydride |
| | | Solvent: | Methanol |
| | | Catalyst: | Acetic acid |
| | | Compound of Formula IX (IV): | 2-(1-methyl)neopentyl-1-benzoylhydrazine |
| | | Compound of Formula V: | 2-bromobenzoylchloride |
| | | Base: | Sodium hydroxide |
| | | Solvent: | Toluene and water |

As previously noted, the compounds of the present invention exhibit excellent insecticidal activity and are selective against insects of the orders Lepidoptera and Coleoptera.

In general, for the control of insects in agriculture, horticulture and forestry, the compounds of the present invention may be used at a dosage corresponding to from about 10 grams to about 10 kilograms of the active substance per hectare and from about 100 grams to about 5 kilograms per hectare of the active substance is preferred. The exact amount of dosage for a given situation can be routinely determined and depends on a variety of factors, for example, the substance used, the kind of insect, the formulation used, the state of the crop infested with the insect and the prevailing weather conditions. The term "insecticidal" as employed in the specification and claims of this application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The compounds of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations," (1973), edited by Wade Van Valkenburg. In these compositions and formulations, the active substance or substances are mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to the target pest, that includes at least one lethal or non-lethal toxicant. Lethal toxicants kill the pest upon ingesting the bait while non-lethal toxicants change the behavior, feeding habits and physiology of the pest for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolysates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1% and 99% by weight, and preferably between about 1% and 75% by weight, of the mixture. Carrier composition mixtures suitable for direct application or field application generally contemplate those in which the active compound is used in an amount substantially between about 0.0001% and 5%, preferably between about 0.001% and 3%, by weight of the mixture. Thus the present invention contemplates overall formulations and compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant (e.g., a surface-active agent, such as an emulsifying agent and/or a dispersing agent), and an amount of the active compound generally, between about 0.0001% and about 99% by weight of the composition, preferably between about 0.001% and about 90% by weight of the composition, and more preferably between about 0.01% and about 75% by weight of the composition, which is effective for the purpose in question. The active compounds can be applied as sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few liters per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of killing, combatting or controlling insects, which comprises contacting insects with a correspondingly combative or toxic amount (i.e., an insecticidally effective amount) of at least one active compound of the invention alone or together with a carrier vehicle (composition or formulation) as noted above. The term "contacting" as employed in the specification and claims of this application is to be construed as applying to at least one of (a) such insects and (b) the corresponding habitat thereof (i.e., the locus to be protected, for example, to a growing crop or to an area where a crop is to be grown) the active compound of this invention alone or as a constituent of a composition or formulation. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example, pumice and attaclay), or chopped tobacco stems or the like.

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e., preparations which when burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol cellulose derivatives or other colloidal materials, such as casein, to improve the adherence of this pesticide to the surface to be protected.

Representative preparation of compositions and formulations including the compounds of the present invention are set forth below as Examples A through I by way of illustration but not limitation.

| Example A Granular | |
|---|---|
| Ingredient | %/wt. |
| Toxicant and toxicant impurities | 0.25 |
| Triton ® X-305 (binder) (Octylphenyl-30-ethylene oxide ethanol) | 0.25 |
| Agsorb ® 24/48 (diluent) (Montmorillonite clay) | 99.50 |

Preparation: The toxicant and Triton ® X-305 are dissolved into methylene chloride and the mixture is added to the Agsorb ® with continuous mixing. The methylene chloride is then allowed to evaporate.

| Example B Dust | |
|---|---|
| Ingredient | %/wt. |
| Toxicant and toxicant impurities | 1.0 |
| Talc | 99.0 |

Preparation: Toxicant is dissolved in excess acetone and the mixture is impregnated onto the talc. The acetone is then permitted to evaporate.

| Example C Wettable Powder | |
|---|---|
| Ingredient | %/wt. |
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| Barden clay (diluent) | 31.7 |
| HiSil ® 233 (diluent) (Sodium silica) | 30.0 |

Preparation: The toxicant, optionally dissolved in a volatile solvent, is absorbed onto the Barden clay and HiSil ® carriers. The Duponal ® and Reax ® are then added and the entire dry mixture blended until homogeneous. The composition is then micronized to a fine particle size.

Example D
Emulsifiable Concentrate

| Ingredient | %/wt. |
|---|---|
| Toxicant and toxicant impurities | 15.0 |
| Sponto ® 232T (emulsifier) (Anionic and nonionic blend of the following surfactants: calcium dodecyl benzene sulfonate; and ethoxylated alkylphenol) | 6.0 |
| Sponto ® 234T (emulsifier) (Anionic and nonionic blend of the following surfactants: calcium dodecyl benzene sulfonate; and ethoxylated alkylphenol) | 4.0 |
| Cyclohexanone (solvent) | 22.5 |
| Tenneco ® 500-100 (solvent) (Aromatic solvent mixture principally comprising xylene, cumene and ethyl benzene having a boiling point range of 290–345° F.) | 52.5 |

Preparation: All ingredients are mixed together with continuous agitation until a homogeneous clear solution is obtained.

Example E
Aerosol

| Ingredient | %/wt. |
|---|---|
| Toxicant and toxicant impurities | 0.5 |
| Freon 12 | 99.5 |

Preparation: The components are mixed and packaged under pressure in a suitable container equipped with a release spray valve.

Example F
Fumigating Candle or Fumigating Powder

| Ingredient | %/wt. |
|---|---|
| Toxicant and toxicant impurities | 1.0 |
| Wood dust | 96.0 |
| Starch | 3.0 |

Preparation: Toxicant, wood dust, and starch are blended together and then molded into a candle using a small amount of water to activate the starch.

Example G
Bait
Method A

| Ingredient | %/wt. |
|---|---|
| Toxicant and toxicant impurities | 1.00 |
| Wheat Bran (carrier and attractant) | 89.95 |
| Corn Syrup (attractant) | 7.00 |
| Corn Oil (attractant) | 2.00 |
| Kathon ® 4200 (preservative) (3-isothiazolone) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

Method B

| Ingredient | %/wt. |
|---|---|
| Toxicant and toxicant impurities | 0.06 |
| Granulated Sugar (carrier and attractant) | 99.94 |

EXAMPLE H

Pellet

Same as Example G, Method A, with this addition: the bait composition is formed into ¼" diameter by ⅜" long pellets using a suitable die and press apparatus.

Example I
Flowable

| Ingredient | %/wt. |
|---|---|
| Toxicant and toxicant impurities | 31.3 |
| Duponal ® WA Dry (wetter) (Sodium lauryl sulfate) | 2.0 |
| Reax ® 45A (dispersant) (Sodium lignin sulfonate) | 5.0 |
| HiSil ® 233 (diluent) (Sodium silica) | 30.0 |
| Kelzan ® (thickener) (Xanthan gum) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparations and may give rise to synergism.

The following known insecticidal, fungicidal and acaricidal compounds are suitable for use in such a combined preparation.

Insecticides such as:

Chlorinated hydrocarbons, for example, 2,2-bis(p-chlorophenyl)-1,1,1-trichloroethane and hexachloroepoxyoctahydrodimethanonaphthalene;

Carbamates, for example, N-methyl-1-napthylcarbamate;

Dinitrophenols, for example, 2-methyl-4,6-dinitrophenol and 2-(2-butyl)-4,6-dinitrophenyl-3,3-dimethylacrylate;

Organic phosphorus compounds, such as dimethyl-2-methoxy-3-carbonyl-1-methylvinyl phosphate, 0,0-diethyl-0-p-nitrophenylphosphorothioate; N-monomethylamide of 0,0-dimethyldithiophosphorylacetic acid;

Diphenylsulfides, for example, p-chlorobenzyl or p-chlorophenyl sulfide and 2,4,4',5-tetrachlorodiphenylsulfide;

Diphenylsulfonates, for example, p-chlorophenylbenzenesulfonate;

Methylcarbinols, for example, 4,4-dichloro-1-trichloromethylbenzhydrol;

Quinoxaline compounds, such as methylquinoxaline dithiocarbonate;

Amidines such as N'-(4-chloro-2-methylphenyl) N,N-dimethylformamidine;

Pyrethroids such as Allethrin;

Biologicals such as *Bacillus thuringiensis* preparations;

Organic tin compounds such as tricyclohexyltin hydroxide;

Synergists such as piperonyl butoxide.

Fungicides such as:

Organic mercury compounds, for example, phenylmercuryacetate and methylmercurycyanoguanide;

Organic tin compounds, for example, triphenyltin hydroxide and triphenyltin acetate; Alkylenebisdithiocarbamates, for example, zinc ethylenebisthiocarbamate and manganese ethylenebisdithiocarbamate; and 2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitrile, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

BIOLOGICAL ACTIVITY

It has been found by biological evaluation that compounds according to the present invention have pesticidal activity and are capable of controlling larvae and adult forms of pests, especially insects from the orders Lepidoptera and Coleoptera and most especially insects from the order Lepidoptera. One skilled in the art will know how to determine the activity of a given compound against a given insect and the dosage required to obtain general or selective insecticidal effects. The compounds of the present invention in part affect the normal development of insects, particularly insects from the order Lepidoptera, by directly and/or indirectly influencing the moulting process.

As previously noted, the compounds of the present invention are particularly suitable for controlling plant destructive insects in crops of cultivated plants, such as, but not limited to, cotton, vegetables, corn and other cereals and the like; forestry, such as, but not limited to, birch, spruce, pine, fir and the like; and ornamental plants, flowers and trees. Compounds of the present invention are also particularly suitable for controlling insects destructive to stored commodities such as seeds and the like; fruit crops, such as, but not limited to fruit and/or citrus trees, raspberry bushes and the like; and turf, such as, but not limited to, lawns, sod and the like.

In evaluating the pesticidal activity of the compounds of this invention, the following test procedures were employed.

A test solution containing 600 parts per million (ppm) was made by dissolving the test compound in a solvent (acetone:methanol, 1:1), adding water to give an acetone:methanol:water system of 5:5:90 and then a surfactant. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Initial evaluations were made on one or more of the following pests:

| Code Symbol | Common Name | Latin Name |
|---|---|---|
| SAW | Southern Armyworm | *Spodoptera eridania* |
| MBB | Mexican Bean Beetle | *Epilachna varivestis* |
| BW | Boll Weevil | *Anthonomus grandis grandis* |

For the foliar bean beetle and armyworm tests, individual bean (*Phaseolus limensis* var. Woods' Prolific) leaves are placed on moistened pieces of filter paper in Petri dishes. The leaves are then sprayed with the test solution using a rotating turntable and allowed to dry. The dishes are infested with 10 third instar larvae of Southern armyworm or Mexican bean beetle. The dishes are then covered.

For the Boll Weevil test ten adult weevils are placed in a 0.5 pint glass Mason jar containing a small cube of apple. The weevils are confined to the jars by fiberglass screen mesh secured by a screw-type rim cap. The jars are then sprayed with the test solution using a rotating turntable, directing the spray through the mesh into the jar.

The percent mortality for the bean beetle, armyworm and boll weevil evaluations are determined 48 hours after treatment. A second observation 96 hours after treatment may be made in the discretion of the experimenter if it is believed the effect of a test compound may not be complete or moribund insects appear to evidence some signs of recovery. Evaluations are based on a scale of 0–100 percent in which 0 equals no activity and 100 equals total kill.

The rotating turntable consists of a fixed, continuously operating spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Illinois) air atomizing nozzle equipped with a No. 2850 fluid cap and No. 70 air cap. At the 10 psig air pressure used and with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75°–80° F. under continuous fluorescent light in a well-ventilated room.

For soil treatment (systemic) trials, a portion of the 600 ppm test solution is diluted to 150 ppm. Ten (10) ml of the 150 ppm test solution is pipetted into soil (approximately 200 g of standard greenhouse soil) in a 3-inch pot containing a lima bean seedling. This results in a soil concentration of approximately 8 ppm. Treated plants are maintained under existing greenhouse conditions for one week. Two bean leaves are removed and placed individually on moist filter paper in Petri dishes. One leaf is infested with 10 third instar larvae of Mexican bean beetle. The other leaf is infested with 10 third instar larvae of Southern armyworm. The dishes are then covered and held for 3 days at which time the percent control (mortality) is determined. A second observation may be made 6 days after infesting the dishes if the experimenter feels the effect may not be complete or moribund insects appear to evidence signs of some recovery. Where necessary, untreated bean leaves are introduced into dishes held for a second observation to preclude insect starvation.

The results of the initial insecticidal evaluations are given in Table IV.

Armyworm and bean beetle spray (foliar) results are 96 hour observations unless otherwise noted. Boll weevil spray results are 48 hour observations unless, in the discretion of the experimenter, particular evaluations were held for 96 hour observations. If, after 96 hours, there was a change in the percent control, it is shown in parentheses. Soil treatment results are 72 hour observations. At the discretion of the experimenter, particular evaluations were held for 144 hour observations. If, after 144 hours, there was a change in the percent control, it is shown in parentheses.

TABLE IV

| | Initial Biological Evaluations | | | | |
|---|---|---|---|---|---|
| | Foliar Application Test Species | | | Soil Application Test Species | |
| Example No. | SAW | MBB | BW | MBB | SAW |
| 1 | 100[a] | 0 | 0 | 80 | 0 |
| 2 | 100 | 0 | 0 | 20 | 0 |
| 3 | 100 | 60[a] | 0 | 100 | 100 |
| 4 | 100 | 0 | 0 | 60 | 0 |
| 5 | 100 | 0 | 0 | 50 | 0 |
| 6 | 40 | 0 | 0 | —[b] | — |
| 7 | 100 | 0 | 0 | 50 | 0 |
| 8 | 10 | 0 | 0 | — | — |
| 9 | 100 | 0 | 0 | 70 | 100 |
| 10 | 100 | 0 | 0 | 60 | 0 |
| 11 | 100 | 0 | 0 | 20 | 100 |
| 12 | 0 | 100 | 0 | 50 | 0 |
| 13 | 100 | 0 | 0 | 20 | 100 |
| 14 | 0 | 0 | 0 | — | — |
| 15 | 100 | 0 | 0 | 20 | 0 |
| 16 | 100 | 0 | 0 | 30 | 100 |
| 17 | 100 | 0 | 0 | 40 | 100 |
| 18 | 100 | 100 | 0 | 100 | 100 |
| 19 | 100 | 0 | 100 | 20 | 0 |
| 20 | 100 | 0 | 0 | — | — |
| 21 | 100 | 0 | 0 | — | — |
| 22 | 100 | 0 | 0 | 40 | 100 |
| 23 | 100 | 0 | 100 | — | — |
| 24 | 100 | 0 | 80 | — | — |
| 25 | 100 | 0 | 0 | — | — |
| 26 | 100 | 100 | 0 | 0 | 100 |
| 27 | 0 | 0 | 0 | — | — |
| 28 | 10 | 0 | 0 | — | — |
| 29 | 100 | 0 | 0 | 0 | 40 |
| 30 | 100 | 0 | 0 | 10 | |
| 31 | 100 | 100 | 0 | 40 | 100 |
| 32 | 0 | 0 | 0 | — | — |
| 33 | 100 | 40 | 0 | 20 | 0 |
| 34 | 100 | 20 | 0 | 70 | 100 |
| 35 | 100 | 100 | 0 | 100 | 100 |
| 36 | 100 | 100 | 20 | 90 | 100 |
| 37 | 100 | 0 | 0 | — | — |
| 38 | 100 | 90 | 20 | 0(60) | 100 |
| 39 | 100 | 0 | 0 | 0 | 20 |
| 40 | 40 | 20 | 20 | 0 | 0 |
| 41 | 100 | 0 | 20 | 20 | 100 |
| 42 | 100 | 100 | 0 | 100 | 100 |
| 43 | 100 | 100 | 0 | 100 | 100 |
| 44 | 100 | 10 | 0 | 0(20) | 0 |
| 45 | 100 | 0 | 0 | 0(40) | 0(40) |
| 46 | 100 | 0 | 60 | 40(80) | 60(80) |
| 47 | 100 | 100 | 0 | 80(90) | 100 |
| 48 | 100 | 100 | 0(40) | 40(60) | 100 |
| 49 | 100 | 100 | 40(80) | 10(60) | 100 |
| 50 | 100 | 0 | 40(80) | 40(70) | 0(10) |
| 51 | 100 | 100 | 0 | 70(100) | 30 |
| 52 | 100 | 100 | 0 | 20(30) | 20(50) |
| 53 | 100 | 0 | 40 | 20(60) | 100 |
| 54 | 100 | 20 | 0 | 0 | 0 |
| 55 | 100 | 10 | 0 | 0 | 0 |
| 56 | 100 | 100 | 0 | 60(80) | 100 |
| 57 | 100 | 0 | 0 | 40(60) | 0 |
| 58 | 100 | 20 | 0 | 20 | 0 |
| 59 | 100 | 70 | 20 | 20 | 100 |
| 60 | 100 | 40 | 0 | 0 | 0 |
| 61 | 0 | 0 | 0 | 60(80) | 0 |

TABLE IV-continued

| | Initial Biological Evaluations | | | | |
|---|---|---|---|---|---|
| | Foliar Application Test Species | | | Soil Application Test Species | |
| Example No. | SAW | MBB | BW | MBB | SAW |
| 62 | 100 | 40 | 0 | 20 | 100 |
| 63 | 100 | 10 | 0 | 20 | 0 |
| 64 | 100 | 20 | 0 | 0(100) | 10(50) |
| 65 | 100 | 20 | 0 | 0(40) | 100 |
| 66 | 100 | 70 | 0 | 40(80) | 40(50) |
| 67 | 100 | 40 | 0 | 20(80) | 100 |
| 68 | 100 | 10 | 20 | 20 | 0 |
| 69 | 100 | 40 | 0 | 20 | 0 |
| 70 | 100 | 40 | 20 | 0(20) | 0 |
| 71 | 0 | 60 | 0 | 0(20) | 0 |
| 72 | 60 | 0 | 0 | 20 | 0 |
| 73 | 100 | 100 | 0 | 40(80) | 100 |
| 74 | 100 | 80 | 0 | 20 | 0 |
| 75 | 100 | 60 | 0 | 0 | 0 |
| 76 | 100 | 60 | 0 | 0(20) | 0 |
| 77 | 100 | 100 | 0 | 0 | 0 |
| 78 | 90 | 40 | 0 | 20 | 0 |
| 79 | 0 | 0 | 20 | 0 | 0 |
| 80 | 0 | 0 | 20 | 0 | 0 |
| 81 | 100 | 0 | 20 | 0 | 20 |
| 82 | 100 | 0 | 0 | 0 | 0 |
| 83 | 100 | 100 | 0 | 60(100) | 100 |
| 84 | 10 | 0 | 0 | 0 | 0 |
| 85 | 100 | 30 | 0 | 0 | 20 |
| 86 | 100 | 30 | 20 | 0 | 80(100) |
| 87 | 100 | 40 | 40 | 0 | 40(50) |
| 88 | 100 | 20 | 0 | 0 | 0 |
| 89 | 100 | 0 | 0 | 0 | 100 |
| 90 | 100 | 0 | 0 | 0 | 90 |
| 91 | 0 | 0 | 40 | 0 | 0 |
| 92 | 100 | 50 | 0 | 0 | 90(100) |
| 93 | 100 | 0 | 0 | 0 | 0 |
| 94 | 0 | 10 | 0 | 0 | 0 |
| 95 | 100 | 100 | 20 | 40(100) | 100 |
| 96 | 100 | 30 | 0 | 0 | 0 |
| 97 | 100 | 0 | 20 | 0 | 0 |
| 98 | 100 | 0 | 0 | 0 | 100 |
| 99 | 100 | 60 | 0 | 40(80) | 100 |
| 100 | 100 | 100 | 0 | 80(100) | 100 |
| 101 | 0 | 0 | 0 | 20 | 0 |
| 102 | 100 | 0 | 0 | 20 | 0(40) |
| 103 | 100 | 100 | 0 | 0(60) | 100 |
| 104 | 100 | 0 | 0(20) | 0 | 40(100) |
| 105 | 100 | 0 | 40 | 0 | 100 |
| 106 | 80 | 0 | 60 | 0 | 0(100) |
| 107 | 100 | 0 | 0 | 0(40) | 100 |
| 108 | 100 | 0 | 0 | 0 | 0 |
| 109 | 100 | 20 | 0 | 0(100) | 100 |
| 110 | 100 | 70 | 0 | 100 | 90(100) |
| 111 | 100 | 100 | 0 | 0 | 0 |
| 112 | 100 | 100 | 20 | 20(40) | 90(100) |
| 113 | 100 | 100 | 0 | 100 | 100 |
| 114 | 100 | 0 | 0 | 0 | 10 |
| 115 | 100 | 100 | 0 | 20(60) | 90(100) |
| 116 | 100 | 10 | 0 | 0 | 0 |
| 117 | 100 | 10 | 0 | 40(80) | 100 |
| 118 | 100 | 10 | 0 | 0 | 90(100) |
| 119 | 100 | 0 | 0 | 0 | 0 |
| 120 | 100 | 30 | 20 | 0 | 0 |
| 121 | 100 | 100 | 0 | 20(40) | 100 |
| 122 | 70 | 20 | 0 | 0 | 20(50) |
| 123 | 100 | 0 | 0 | 0(100) | 100 |
| 124 | 100 | 100 | 0 | 0 | 20(30) |
| 125 | 100 | 0 | 0 | 0 | 0 |
| 126 | 100 | 10 | 0 | 0 | 0 |
| 127 | 100 | 10 | 0 | 20 | 0 |
| 128 | 100 | 0 | 0 | 0 | 0 |
| 129 | 100 | 40 | 40(60) | 100(80) | 80(100) |
| 130 | 100 | 0 | 0 | 0(20) | 100 |
| 131 | 100 | 0 | 0 | 0 | 100 |
| 132 | 100 | 0 | 0 | 20(40) | 0 |
| 133 | 100 | 10 | 0 | 0 | 0 |
| 134 | 100 | 10 | 0 | 0 | 10(30) |
| 135 | 100 | 0 | 0 | 20(40) | 60 |
| 136 | 100 | 70 | 0 | 20 | 30(50) |
| 137 | 100 | 10 | 0 | 40(60) | 0 |
| 138 | 100 | 0 | 0 | 0 | 90(100) |

TABLE IV-continued

| | Initial Biological Evaluations | | | | |
| --- | --- | --- | --- | --- | --- |
| | Foliar Application Test Species | | | Soil Application Test Species | |
| Example No. | SAW | MBB | BW | MBB | SAW |
| 139 | 100 | 0 | 0 | 0(20) | 0 |
| 140 | 100 | 0 | 0 | 20 | 0 |
| 141 | 100 | 100 | 0 | 20(100) | 100 |
| 142 | 100 | 0 | 0 | 20 | 40 |

[a]48 hour observation
[b]No data reported

It should be understood that the instant specification and examples are set forth by way of illustration and not limitation, and that various modifications and changes may be made without departing from the spirit and scope of the present invention as defined by the appended claims.

We claim:

1. A method of controlling insects which comprises contacting the insects with an insecticidally effective amount of a compound having the formula $$A-\underset{H}{\overset{X}{\underset{\|}{C}}}-N-\underset{R^1}{N}-\overset{X'}{\underset{\|}{C}}-B$$

wherein
X and X' are the same or different O or S;
$R^1$ is unsubstituted ($C_3$–$C_{10}$) branched alkyl or ($C_1$–$C_4$) straight chain alkyl substituted with one or two of the same or different ($C_3$–$C_6$)cycloalkyl; and
A and B are the same or different unsubstituted naphthyl or substituted naphthyl where the substituents can be from one to three of the same or different halo; cyano; nitro; hydroxy; ($C_1$–$C_4$)alkoxy; ($C_1$–$C_4$)alkyl; carboxy; ($C_1$–$C_4$)alkoxycarbonyl; or ($C_1$–$C_4$)alkanoyloxy; or unsubstituted phenyl or substituted phenyl where the substituents can be from one to three of the same or different halo; nitro; cyano; hydroxy; ($C_1$–$C_6$)alkyl; ($C_1$–$C_6$)haloalkyl; ($C_1$–$C_6$)cyanoalkyl; ($C_1$–$C_6$)alkoxy; ($C_1$–$C_6$)alkoxyalkyl having independently the stated number of carbon atoms in each alkyl group; carboxy; ($C_1$–$C_6$)alkoxycarbonyl; ($C_1$–$C_6$)alkanoyloxy; sulfhydryl; ($C_1$–$C_6$)thiocyanatoalkyl; thiocyanato; ($C_1$–$C_6$)alkylthio; sulfinyl; sulfonyl; sulfonate; phenyl or phenoxy; and agronomically acceptable salts thereof.

2. The method of claim 1 wherein
X and X' are O or S;
$R^1$ is unsubstituted ($C_3$–$C_8$) branched alkyl or ($C_1$–$C_4$) straight chain alkyl substituted with one or two of the same or different ($C_3$–$C_4$)cycloalkyl;
A and B are the same or different unsubstituted naphthyl; or unsubstituted phenyl or substituted phenyl where the substituents can be from one to three of the same or different halo; nitro; cyano; ($C_1$–$C_5$)alkyl; ($C_1$–$C_2$)haloalkyl; ($C_1$–$C_2$)cyanoalkyl; hydroxy; ($C_1$–$C_2$)alkoxy; ($C_1$–$C_2$)alkoxyalkyl having independently the stated number of carbon atoms in each alkyl group; carboxy; ($C_1$–$C_2$)alkoxycarbonyl; ($C_1$–$C_2$)alkanoyloxy; ($C_1$–$C_2$)thiocyanatoalkyl; phenyl or phenoxy; and agronomically acceptable salts thereof.

3. The method of claim 2 wherein
X and X' are O;
$R^1$ is branched ($C_4$–$C_7$) alkyl; and
A and B are the same or different unsubstituted phenyl or substituted phenyl where the substituents can be from one to three of the same or different halo, nitro, ($C_1$–$C_4$)alkyl, or ($C_1$–$C_2$)alkoxy,; and agronomically acceptable salts thereof.

4. The method of claim 3 wherein
X is X' are O;
$R^1$ is t-butyl, neopentyl (2,2-dimethylpropyl) or 1,2,2-trimethylpropyl; and
A and B are the same or different unsubstituted phenyl or substituted phenyl where the substituents can be one or two of the same or different chloro, fluoro, bromo, iodo, nitro, methyl, ethyl, methoxy or trifluoromethyl; and
agronomically acceptable salts thereof.

5. The method of claim 4 wherein the compound is applied at from about 10 grams to about 10 kilograms per hectare.

6. The method of claim 4 wherein the compound is applied at from about 100 grams to about 5 kilograms per hectare.

7. The method of claim 4 wherein the compound is N'-t-butyl-N-(4-methylbenzoyl)-N'-(4-chlorobenzoyl)hydrazine.

8. The method of claim 4 wherein the compound is N'-t-butyl-N-benzoyl-N'-(4-chlorobenzoyl)hydrazine.

9. The method of claim 64 wherein the compound is N'-t-butyl-N-benzoyl-N'-(4-fluorobenzoyl)hydrazine.

10. The method of claim 4 wherein the compound is N'-t-butyl-N-(4-methylbenzoyl)-N'-(3-methylbenzoyl)hydrazine.

11. The method of claim 4 wherein the compound is N'-t-butyl-N,N'-dibenzoyl hydrazine.

12. The method of claim 4 wherein the compound is N'-t-butyl-N-benzoyl-N'-(2-methoxybenzoyl)hydrazine.

13. The method of claim 4 wherein the compound is N'-t-butyl-N-benzoyl-N'-(3-chlorobenzoyl)hydrazine.

14. The method of claim 4 wherein the compound is N'-t-butyl-N-benzoyl-N'-(3-fluorobenzoyl)hydrazine.

15. The method of claim 4 wherein the compound is N'-t-butyl-N-(4-ethylbenzoyl)-N'-(3-methylbenzoyl)hydrazine.

16. The method of claim 4 wherein the compound is N'-t-butyl-N-benzoyl-N'-(3,5-dichlorobenzoyl)hydrazine.

17. The method of claim 4 wherein the compound is N'-t-butyl-N-(2-methylbenzoyl)-N'-benzoylhydrazine.

18. The method of claim 4 wherein the compound is N'-t-butyl-N-(4-chlorobenzoyl)-N'-(2-chlorobenzoyl)hydrazine.

19. The method of claim 4 wherein the compound is N'-t-butyl-N-benzoyl-N'-(2-bromobenzoyl)hydrazine.

20. The method of claim 4 wherein the compound is N'-t-butyl-N-benzoyl-N'-(3,4-dichlorobenzoyl)hydrazine.

21. The method of claim 4 wherein the compound is N'-t-butyl-N-(4-chlorobenzoyl)-N'-(3,5-dichlorobenzoyl)hydrazine.

22. The method of claim 4 wherein the compound is N'-t-butyl-N-(4-chlorobenzoyl)-N'-(3-chlorobenzoyl)hydrazine.

23. The method of claim 4 wherein the compound is N'-t-butyl-N-(2-chlorobenzoyl)-N'-benzoylhydrazine.

24. The method of claim 4 wherein the compound is N'-t-butyl-N,N'-bis(2-fluorobenzoyl)hydrazine.

25. The method of claim 4 wherein the compound is N'-t-butyl-N-(4-chlorobenzoyl)-N'-benzoylhydrazine.

26. The method of claim 4 wherein the compound is N'-t-butyl-N,N'-bis(2-chlorobenzoyl)hydrazine.

27. The method of claim 4 wherein the compound is N'-t-butyl-N-benzoyl-N'-(2-nitrobenzoyl)hydrazine.

28. The method of claim 4 wherein the compound is N'-t-butyl-N-(3-chlorobenzoyl)-N'-benzoylhydrazine.

29. The method of claim 4 wherein the compound is N'-t-butyl-N-benzoyl-N'-(4-ethylbenzoyl)hydrazine.

30. The method of claim 4 wherein the compound is N'-(1,2,2-trimethylpropyl)-N-benzoyl-N'-(2-nitrobenzoyl)hydrazine.

31. The method of claim 4 wherein the compound is N'-t-butyl-N-benzoyl-N'-(2,4-dichlorobenzoyl)hydrazine.

32. The method of claim 4 wherein the compound is N'-t-butyl-N-benzoyl-N'-(2-fluorobenzoyl)hydrazine.

33. The method of claim 4 wherein the compound is N'-t-butyl-N-(4-chlorobenzoyl)-N'-(2,4-dichlorobenzoyl)hydrazine.

34. The method of claim 4 wherein the compound is N'-t-butyl-N-benzoyl-N'-(2-chlorobenzoyl)hydrazine.

35. The method of claim 3 wherein the compound is applied at from about 10 grams to about 10 kilograms per hectare.

36. The method of claim 3 wherein the compound is applied at from about 100 grams to about 5 kilograms per hectare.

37. The method of claim 3 wherein the compound is applied as a constituent of a composition comprising an insecticidally effective amount of said compound and an agronomically acceptable carrier.

38. The method of claim 4 wherein the compound is applied as a constituent of a composition comprising an insecticidally effective amount of said compound and an agronomically acceptable carrier.

39. The method of claim 2 wherein the compound is applied at from about 10 grams to about 10 kilograms per hectare.

40. The method of claim 2 wherein the compound is applied at from about 100 grams to about 5 kilograms per hectare.

41. The method of claim 2 wherein the insects are from the order Lepidoptera.

42. The method of claim 41 wherein when A is $-C_6H_4C(CH_3)_3-4$, B is not $-C_6H_4C(CH_3)_3-4$.

43. The method of claim 42 wherein when A is $-C_6H_5$, B is not $-C_6H_4OSO_2CH_3-4$; and when A is $-C_6H_4Cl-4$, B is not $-C_6H_4CH_2Cl-4$.

44. The method of claim 43 wherein the compound is applied to plants.

45. The method of claim 2 wherein the insects are from the order Coleoptera.

46. The method of claim 45 wherein when A is $-C_6H_5$, B is not $-C_6H_4OCH_3-4$, $+-C_6H_4C(CH_3)_3-4$, $-C_6H_4OH-4$ or $-C_6H_4Br-3$; when A is $-C_6H_5Cl-4$, B is not $-C_6H_4CH_3-3$ or $-C_6H_4CH_2Cl-3$; when A is $-C_6H_4NO_2-4$, B is not $-C_6H_4NO_2-4$; when A is $-C_6H_4CN-4$, B is not $-C_6H_4CN-4$; when A is $-C_6H_3Cl_2-3,5$, B is not $-C6H3Cl_2-+3,5$; when A is $-C_6H_4CF_3-4$, B is not $-C_6H_3Cl_2-3,4$; when A is $-C6+H_4CH_2CH_3-4$, B is not $-C_6H_4Cl-4$; and when A is $-C_6H_4Br$, B is not $-C_6H_5$.

47. The method of claim 1 wherein the insects are from the order Lepidoptera.

48. The method of claim 1 wherein the compound is applied at from about 10 grams to about 10 kilograms per hectare.

49. The method of claim 1 wherein the compound is applied at from about 100 grams to about 5 kilograms per hectare.

50. The method of claim 1 wherein the compound is applied to plants or an area where plants are to be grown.

51. The method of claim 50 wherein the compound is applied to allow root absorption and transport by plants.

52. The method of claim 1 wherein the compound is applied as a constituent of a composition comprising an insecticidally effective amount of said compound and an agronomically acceptable carrier.

* * * * *